(12) United States Patent
Little et al.

(10) Patent No.: US 11,660,346 B2
(45) Date of Patent: May 30, 2023

(54) ENGINEERED MICROPARTICLES FOR MACROMOLECULE DELIVERY

(71) Applicant: University of Pittsburgh-Of the Commonwealth System of Higher Education, Pittsburgh, PA (US)

(72) Inventors: Steven R. Little, Pittsburgh, PA (US); Sam N. Rothstein, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 103 days.

(21) Appl. No.: 16/866,221

(22) Filed: May 4, 2020

(65) Prior Publication Data
US 2020/0360518 A1 Nov. 19, 2020

Related U.S. Application Data

(63) Continuation of application No. 15/494,127, filed on Apr. 21, 2017, now abandoned, which is a
(Continued)

(51) Int. Cl.
*G01N 33/48* (2006.01)
*G01N 33/50* (2006.01)
(Continued)

(52) U.S. Cl.
CPC ............ *A61K 47/34* (2013.01); *A61K 9/1647* (2013.01); *A61K 9/1694* (2013.01); *A61K 9/48* (2013.01);
(Continued)

(58) Field of Classification Search
CPC .... A61K 47/34; A61K 9/1647; A61K 9/1694; A61K 9/48; G16B 5/30; G16B 15/00; G16B 50/20; G16B 50/30
See application file for complete search history.

(56) References Cited

U.S. PATENT DOCUMENTS

| 5,603,960 A | 2/1997 | O'Hagan et al. |
| 5,618,563 A | 4/1997 | Berde et al. |

(Continued)

FOREIGN PATENT DOCUMENTS

| WO | WO 2004/043432 | 5/2004 |
| WO | WO 2004/112752 | 12/2004 |

OTHER PUBLICATIONS

Berchane et al., "Effect of mean diameter and polydispersity of PLG microspheres on drug release: experiment and theory," *International Journal of Pharmaceutics* 337(1-2): 118-126, Jan. 7, 2007.
(Continued)

*Primary Examiner* — Russell S Negin
(74) *Attorney, Agent, or Firm* — Klarquist Sparkman, LLP

(57) ABSTRACT

A method for making a modified release composition, comprising:
selecting a desired active agent and polymer matrix for formulating into a modified release composition;
assessing degradation effect on release of the active agent from the composition including plotting polymer molecular weight ($M_{wr}$) at onset of active agent release vs. active agent molecular weight ($M_{wA}$);
predicting performance of multiple potential formulations for the composition based on the degradation assessment and average polymer matrix initial molecular weight ($M_{wo}$) to define a library of building blocks;
determining the optimal ratio of the building blocks to satisfy a specified release profile; and
making a modified release composition based on the optimal ratio determination.

16 Claims, 13 Drawing Sheets

Related U.S. Application Data continuation of application No. 13/395,245, filed as application No. PCT/US2010/048465 on Sep. 10, 2010, now abandoned.

(60) Provisional application No. 61/241,259, filed on Sep. 10, 2009.

(51) Int. Cl.
| | |
|---|---|
| *A61K 47/34* | (2017.01) |
| *A61K 9/16* | (2006.01) |
| *G16B 5/30* | (2019.01) |
| *G16B 15/00* | (2019.01) |
| *G16B 50/20* | (2019.01) |
| *G16B 50/30* | (2019.01) |
| *A61K 9/48* | (2006.01) |

(52) U.S. Cl.
CPC .............. *G16B 5/30* (2019.02); *G16B 15/00* (2019.02); *G16B 50/20* (2019.02); *G16B 50/30* (2019.02)

(56) References Cited

U.S. PATENT DOCUMENTS

| | | | |
|---|---|---|---|
| 6,217,911 | B1 | 4/2001 | Vaugn et al. |
| 6,447,796 | B1 | 9/2002 | Vook et al. |
| 6,596,316 | B2 | 7/2003 | Lyons et al. |
| 2003/0055075 | A1 | 3/2003 | Rubsamen et al. |
| 2003/0185873 | A1 | 10/2003 | Chasin et al. |
| 2006/0034923 | A1 | 2/2006 | Li et al. |
| 2007/0275080 | A1 | 11/2007 | Laulicht et al. |

OTHER PUBLICATIONS

Berchane et al., "Optimization of PLG microspheres for tailored drug release," *International Journal of Pharmaceutics* 383(1-2):81-88, Sep. 11, 2009.

De Villiers et al., "Chapter 5: Drug loading into and in vitro release from nanosized drug delivery systems," *Nanotechnology in Drug Delivery*, pp. 129-162, published 2009 by Springer.

European Extended Search Report from corresponding European Application No. 10816175.3 dated Sep. 17, 2013.

Examination Report issued by European Patent Office for EPC Application No. 10816175.3 dated Jun. 22, 2016, 10 pages.

Examination Report issued for EPC Application No. 10816175.3 dated Dec. 18, 2019.

Grassi et al., "5.2: Dissolution," *Understanding Drug Release and Absorption Mechanisms: A Physical and Mathematical Approach*, ed. Grassi et al., pp. 250-251, 370-371, published 2007 by Taylor & Francis Group, LLC.

Grassi et al., "Mathematical Modelling and Controlled Drug Delivery: Matrix Systems," *Current Drug Delivery* 2(1):97-116, Jan. 1, 2005.

Hammes, ed., *Phyiscal Chemistry for the Biological Sciences*, published 2007 by John Wiley & Sons.

International Search Report and the Written Opinion of the International Searching Authority of International Application No. PCT/US2010/048465, dated Jun. 16, 2011.

Kaowumpai et al., "Development of a 3D Mathematical Model for a Doxorubicin Controlled Release System using Pluronic Gel for Breast Cancer Treatment," *International Journal of Medical, Health, Biomedical Bioengineering and Pharmaceutical Engineering*, 1(8): 489-495, 2007.

Rothstein et al., "A 'tool box' for rational design of degradable controlled release formulations," *Journal of Materials Chemistry* vol. 21, pp. 29-39, Sep. 2, 2010.

Rothstein et al., "A simple model framework for the prediction of controlled release from bulk eroding polymer matrices," *Journal of Materials Chemistry*, 16(18): 1873-1880, Mar. 4, 2008.

Rothstein et al., "A unified mathematical model for the prediction of controlled release from surface and bulk eroding polymer matrices," *Biomaterials* 30(8):1657-64, Mar. 2009 (available online Dec. 19, 2008).

Rothstein et al., "A Unified Mathematical Model for the Prediction of Controlled Release from Surface and Bulk Eroding Matrices," *Biomaterials*, 30(8): 1657-1664, Mar. 2009.

Shoaib et al., "Evaluation of Drug Release Kinetics from Ibuprofen Matrix Tablets Using HPMC," *Pak. J. Pharm. Sci.*, 19(2):119-124, 2006.

Siepmann et al., "HPMC-Matrices for Controlled Drug Delivery: A New Model Combining Diffusion, Swelling, and Dissolution Mechanisms and Predicting the Release Kinetics," *Pharmaceutical Research* 16(11):1748-1756, Nov. 1999.

Siepmann et al., "Hydrophilic Matrices for Controlled Drug Delivery: An Improved Mathematical Model to Predict the Resulting Drug Release Kinetics (the 'Sequential Layer' Model)," *Pharmaceutical Research*, 17(10):1290-1298, Oct. 2000.

Siepmann et al., "Mathematical modeling of bioerodible, polymeric drug delivery systems," *Advanced Drug Delivery Reviews*, 48(2-3): 229-247, May 7, 2001.

Somasi et al., "Implementation of the 'Sequential Layer' Controlled-Release Model," poster presented at 31st Annual Meeting of the Controlled Release Society, The Dow Chemical Company, Jun. 12-15, 2004.

Von Burkersroda et al., "Why degradable polymers undergo surface erosion or bulk erosion," *Biomaterials* 23(21):4221-4231, Aug. 1, 2002.

Wise et al., "Asymmetrical Membrane Film-Coated Dosage Forms," from *Handbook of Pharmaceutical Controlled Release Technology*, 2000, p. 759.

Wu et al., "Mathematical modeling and in vitro study of controlled drug release via a highly swellable and dissoluble polymer matrix: polyethylene oxide with high molecular weights," *Journal of Controlled Release* 102(3):569-581, Feb. 16, 2005.

Time (Day)

Time (Day)

FIG. 9A
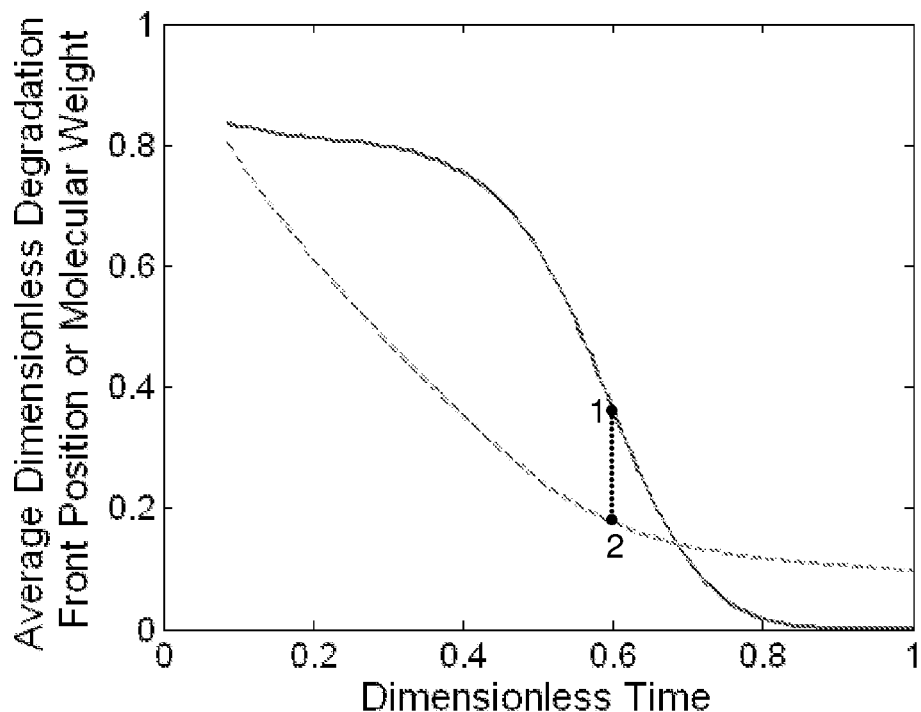
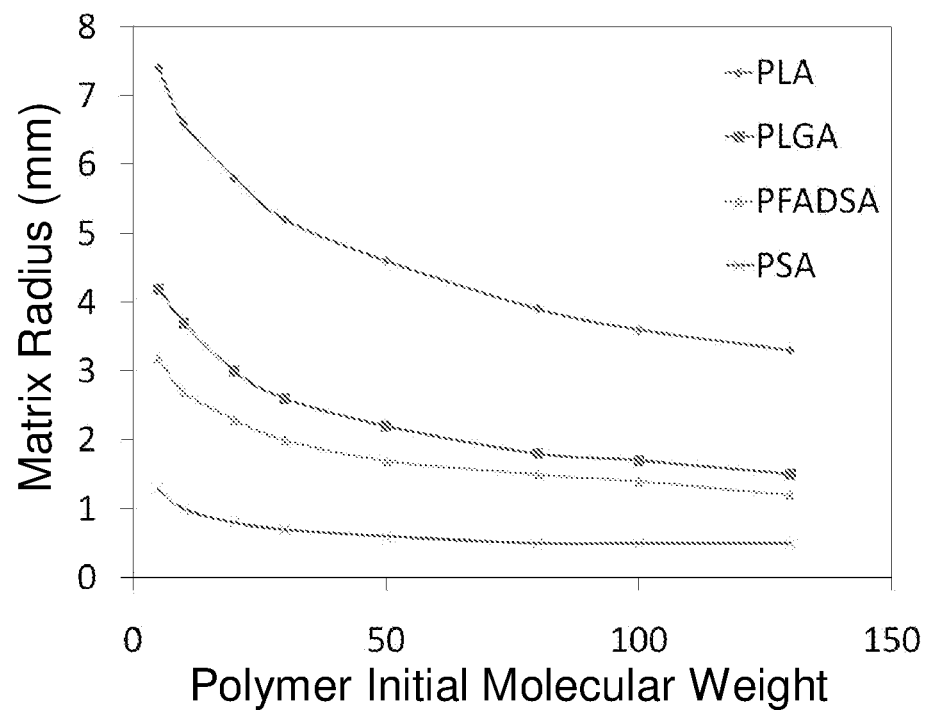
FIG. 9B

FIG. 12A
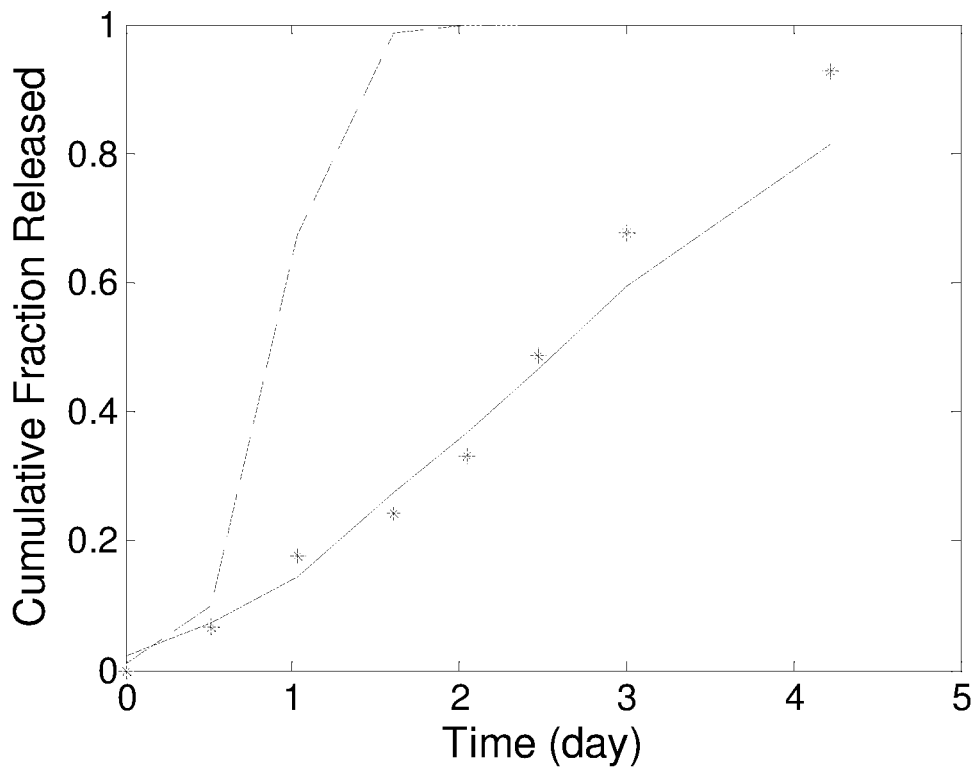
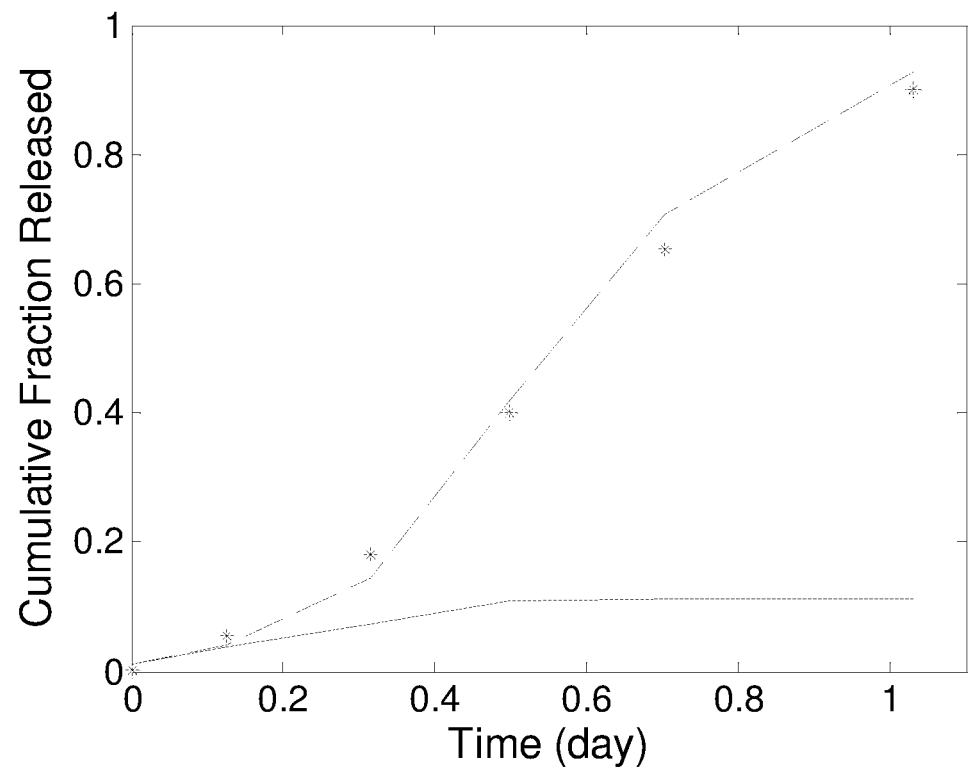
FIG. 12B

ENGINEERED MICROPARTICLES FOR MACROMOLECULE DELIVERY

CROSS-REFERENCE TO RELATED APPLICATIONS

This application is a continuation of U.S. application Ser. No. 15/494,127, filed Apr. 21, 2017, which is a continuation of U.S. application Ser. No. 13/395,245, filed Mar. 9, 2012, which is the U.S. National Stage of International Application No. PCT/US2010/048465, filed Sep. 10, 2010, which was published in English under PCT Article 21(2), which in turn claims the benefit of U.S. Provisional Application No. 61/241,259, filed Sep. 10, 2009, which are incorporated herein by reference in their entirety.

BACKGROUND

Since polymer matrices were first used to protect and deliver drugs, controlled release technology has expanded considerably. At present, a wide variety of biodegradable polymers, encapsulation techniques, and matrix geometries have been employed to deliver agents ranging from small molecule chemotherapeutics to protein vaccines. The wide applicability of polymer matrix-based controlled release technology allows for the development of numerous unique therapeutics, each with the potential to improve patient quality of life through increased patient compliance and more effective administration.

The methods for developing specific therapeutics have, however, changed little since the field of controlled release first began. Although research on controlling the delivery of numerous drugs now abounds, formulating each new therapeutic still requires months of iterative and costly in vitro testing to target a suitable drug release profile. Studying a broad array of literature on bulk eroding polymer matrices shows that this profile can range from linear to four-phase patterns with (1) an initial burst, (2) a lag phase, (3) a secondary burst and (4) a terminal release phase. Further, reports studying these systems debate which, if any one, property, such as the polymer degradation mechanism, matrix crystallinity or others, is the most influential for controlling release.

SUMMARY

Disclosed herein is a method for making a modified release composition, comprising:

selecting a desired active agent and polymer matrix for formulating into a modified release composition;

assessing degradation effect on release of the active agent from the composition including plotting polymer molecular weight ($M_{wr}$) at onset of active agent release vs. active agent molecular weight ($M_{wA}$);

predicting performance of multiple potential formulations for the composition based on the degradation assessment and average polymer matrix initial molecular weight ($M_{wo}$) to define a library of building blocks;

determining the optimal ratio of the building blocks to satisfy a specified release profile; and making a modified release composition based on the optimal ratio determination.

Also disclosed herein is a composition comprising three different populations of sustained release microparticles wherein each microparticle includes at least one active agent and at least one biodegradable polymer matrix, wherein:

the polymer matrix of the first population of microparticles has a $M_W$ of 6.0 to 8.1 kDa and constitutes 15.1 to 33.0% by weight of the composition;

the polymer matrix of the second population of microparticles has a $M_W$ of 9.1 to 12.4 kDa and constitutes 25.7 to 22.8% by weight of the composition; and the polymer matrix of the third population of microparticles has a $M_W$ of 26.8 to 36.4 kDa and constitutes 59.2 to 44.1% by weight of the composition; and wherein the composition can sustain a release of the active agent for at least 1 month.

Further disclosed herein is a composition comprising two different populations of sustained release microparticles, wherein each microparticle includes at least one active agent and at least one biodegradable polymer matrix, wherein:

the polymer matrix of the first population of microparticles has a $M_W$ of 5.1 to 6.8 kDa and constitutes 24.8 to 72.9% by weight of the composition;

the polymer matrix of the second population of microparticles has a $M_W$ of 8.3 to 11.0 kDa and constitutes 75.2 to 27.1% by weight of the composition; and wherein the composition can sustain a release of the active agent for at least 2 weeks.

The foregoing and other objects, features, and advantages of the invention will become more apparent from the following detailed description, which proceeds with reference to the accompanying figures.

BRIEF DESCRIPTION OF THE DRAWINGS

FIG. 8A) surface erosion, FIG. 8B) a transition from surface to bulk erosion and FIG. 8C) bulk erosion. The lifetime of each matrix changes with its size, such that each line in FIG. 8A) represents 1 month, FIG. 8B) represents 1 day and FIG. 8C) represents 2 hours. In each figure, the line furthest to the right and top indicates the earliest time point.

FIGS. 9A-9B are graphs showing the calculation of critical length using a second order rate expression as a function of both the initial molecular weight of polymer and hydrolysis rate constant. FIG. 9A) Critical length (point 2) was calculated as the matrix size (dashed line) in which the average molecular weight of polymer at the degradation front (solid line) decreases most rapidly (point 1), indicating the onset of bulk erosion. FIG. 9B) Values for critical length as a function of initial molecular weight for a variety of polymer matrices: PLA (diamond), 50:50 PLGA (square), 50:50 PFAD:SA (triangle) and PSA (circle).

FIGS. 12A-12B are graphs showing predictions of release from FIG. 12(A) bulk eroding and FIG. 12(B) surface eroding poly(ortho ester) matrices. Predictions have been made for the experimental data for dye release (astricks), while accounting for the hydrolysis of the anhydride excipient, with the complete model (solid line, FIG. 12(A) SSE=0.0237 and FIG. 12(B) SSE=1.1539) and the simplified version which assumes bulk erosion (dashed line, FIG. 12(A) SSE=1.0077 and FIG. 12(B) SSE=0.0061). For calculations in both FIG. 12A and FIG. 12B, the following parameters were used: Mwo=28.2 kDa, $Mw_r$=10.2 kDa, Rp=5 mm, and L=1.4 mm. Based on their differing anhydride contents, values of $D_A$ were unique to FIG. 12 and FIG. 12B, with $D_A$=1.44×$10^{-12}$ m²/s in FIG. 12A and $D_A$=9.75× $10^{-12}$ m²/s in FIG. 12B.

DETAILED DESCRIPTION

Figure 1A:
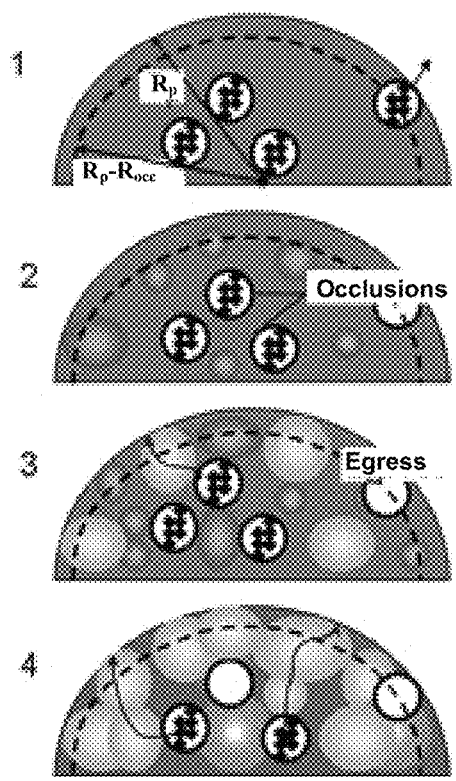
FIGS. 1A and 1B are a schematic depiction of a model paradigm that can account for four-phase release. A) Cross section diagrams depicting the four phases of release for a double emulsion microparticle with agent encapsulated heterogeneously in occlusions. Initially, agent abutting the matrix surface is released (1). The remaining agent requires the growth and coalescence of pores for further egress (2-4). B) Release profile for macromolecular drug encapsulated in biodegradable polymer matrix with four phases of release labeled. The numbers associated with each cross section diagram (A) indicate which phase of the release profile is illustrated. These phases are 1) initial burst, 2) lag phase, 3) secondary burst and 4) final release.

The term "formulation" or "composition" as used herein refers to the drug in combination with pharmaceutically acceptable carriers and additional inert ingredients. This includes orally administrable formulations as well as formulations administrable by other means.

The term "dosage form" as used herein is defined to mean a pharmaceutical preparation in which doses of active drug are included.

"Modified release dosage forms or compositions" as used herein is as defined by the United States Pharmacopoeia (USP) as those whose drug release characteristics of time course and/or location are chosen to accomplish therapeutic or convenience objectives not offered by conventional, immediate release or uncoated normal matrix dosage forms. As used herein, the definition of the term "modified-release" encompasses the scope of the definitions for the terms "extended release", "enhanced-absorption", "controlled release", and "delayed release".

"Controlled release dosage forms" or "control-releasing dosage forms", or dosage forms which exhibit a "controlled release" of the active agent as used herein is defined to mean dosage forms administered once- or twice-daily that release the active agent at a controlled rate and provide plasma concentrations of the active agent that remain controlled with time within the therapeutic range of the active agent over a predetermined time period. "Controlled release" or "control releasing" is defined to mean release of the drug gradually or in a controlled manner per unit time. For example, the controlled rate can be a constant rate providing plasma concentrations of the active agent that remain invariant with time within the therapeutic range of the active agent over a predetermined time period.

"Sustained-release dosage forms" or dosage forms which exhibit a "sustained-release" of the active agent as used herein is defined to mean dosage forms administered once- or twice-daily that provide a release of the active agent sufficient to provide a therapeutic dose soon after administration, and then a gradual release over an extended period of time such that the sustained-release dosage form provides therapeutic benefit over a predetermined time period.

"Extended- or sustained-release dosage forms" or dosage forms which exhibit an "extended or sustained release" of the active agent as used herein is defined to include dosage forms administered once- or twice-daily that release the active agent slowly, so that plasma concentrations of the active agent are maintained at a therapeutic level for an extended period of time such that the extended or sustained-release dosage form provides therapeutic benefit over a predetermined period.

"Delayed-release dosage forms" or dosage forms which exhibit a "delayed release" of the active agent as used herein is defined to mean dosage forms administered once-daily that do not effectively release drug immediately following administration but at a later time. Delayed-release dosage forms provide a time delay prior to the commencement of drug-absorption. This time delay is referred to as "lag time" and should not be confused with "onset time" which represents latency, that is, the time required for the drug to reach minimum effective concentration.

The term "polymer matrix" as used herein is defined to mean a dosage form in which the active agent is dispersed or included within a matrix, which matrix can be a biodegradable polymer.

The term "medicament" as used herein refers to all possible oral and non-oral dosage forms, including but not limited to, all modified release dosage forms, osmosis controlled release systems, erosion controlled release systems, dissolution controlled release systems, diffusion controlled release systems, matrix tablets, enteric coated tablets, single and double coated tablets (including the extended release tablets), capsules, minitablets, caplets, coated beads, granules, spheroids, pellets, microparticles, suspensions, topicals such as transdermal and transmucosal compositions and delivery systems (containing or not containing matrices), injectables, inhalable compositions, and implants.

Variables
$C_A$=Concentration of agent in the polymer matrix
$C_{Ao}$=Initial concentration of agent in the polymer matrix
D=Diffusivity of agent leaving the matrix via pores
$\varepsilon(t)$=Time dependent matrix porosity
$kC_w(n)$=Pseudo-first order degradation rate distribution
$M_{wA}$=Release agent molecular weight
$M_{wo}$=Average polymer initial molecular weight
$M_{wr}$=Molecular weight of release
P(t)=Cumulative fraction of agent retained in the matrix by time t
R(t)=Cumulative fraction of agent released from the matrix by time t
$R_{occ}$=Occlusion radius
$R_p$=Matrix dimension(s) across which diffusive release occurs, e.g. particle radius, or film thickness
t=Time
$\tau(n)$=Distribution of induction times for pore formation
Abbreviations
PLGA=poly(lactic-co-glycolic acid)
PLA=poly(lactic acid) SA=sebacic ahydride CPH=1,6-bis-p-carboxyphenoxy hexane PSA=poly sebacic anhydride
BSA=bovine serum albumin Described herein is a broadly applicable model for predicting controlled release that can eliminate the need for exploratory, in vitro experiments during the design of new biodegradable matrix-based therapeutics. A simple mathematical model has been developed that can predict the release of many different types of agents from bulk eroding polymer matrices without regression. New methods for deterministically calculating the magnitude of the initial burst and the duration of the lag phase (time before Fickian release) were developed to enable the model's broad applicability. To complete the model's development, such that predictions can be made from easily measured or commonly known parameters, two correlations were developed by fitting the fundamental equations to published controlled release data. To test the model, predictions were made for several different biodegradable matrix systems. In addition, varying the readily attainable parameters over rational bounds shows that the model predicts a wide range of therapeutically relevant release behaviors.

In addition, a further set of equations accounts for dissolution- and/or degradation-based release and is dependent upon hydration of the matrix and erosion of the polymer. To test the model's accuracy, predictions for agent egress were compared to experimental data from polyanhydride and poly(ortho ester) implants that were postulated to undergo either dissolution-limited or degradation-controlled release. Because these predictions are calculated solely from readily-attainable design parameters, this model can be used to guide the design controlled release formulations that produce a broad array of custom release profiles.

Consider an initially uniform matrix of known geometry comprised of a biodegradable polymer, such as a polyester or polyanhydride, and with randomly distributed entrapped release agent (e.g. drug of concentration $C_{Ao}$), loaded below its percolation threshold (such that agent remains discrete) to ensure matrix mediated release. This agent can either be dispersed as crystals (such as in the case of uniformly loaded systems, e.g. single emulsion-based particulates) or housed as a solution in occlusions (e.g. double emulsion-based particulates). At time zero, an aqueous reservoir begins to hydrate the matrix, a process which happens quickly for the bulk eroding polymers matrices considered herein. As the matrix hydrates, encapsulated agent adjacent to the matrix surface (with a direct pathway for egress) diffuses into the reservoir in a phase typically dubbed "the initial burst" (see FIG. 1, phase 1). The relative size of the occlusion ($R_{occ}$) occupied by the encapsulated agent is proportional to the magnitude of the initial burst as illustrated in FIG. 2.

Figure 1B:
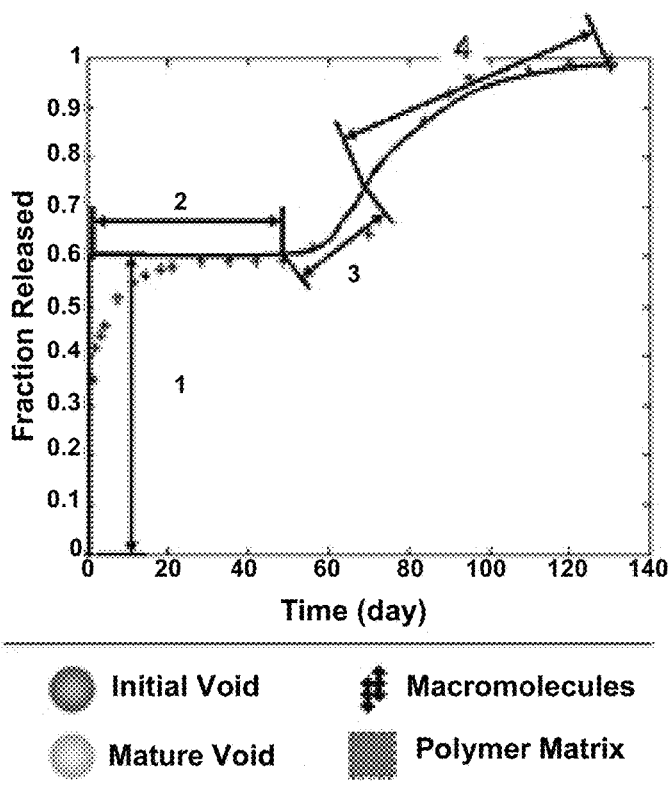
Figure 2A:
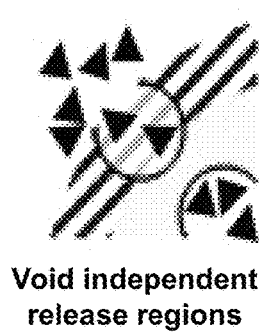
FIGS. 2A and 2B are a schematic depiction of the initial burst as it relates to occlusion size. A) The double emulsion particle contains large occlusions filled with drug solution and produces a significant initial burst. B) The more uniformly loaded (e.g. single emulsion particle, melt cast matrix) contains small granules of drug and has minimal initial release.
Figure 2A:
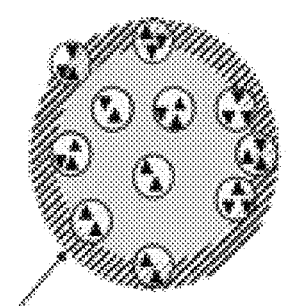
Figure 2A:
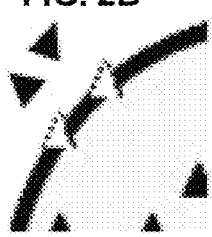
Figure 2A:
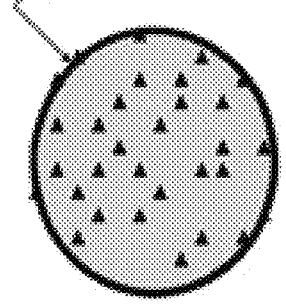
Figure 2B:
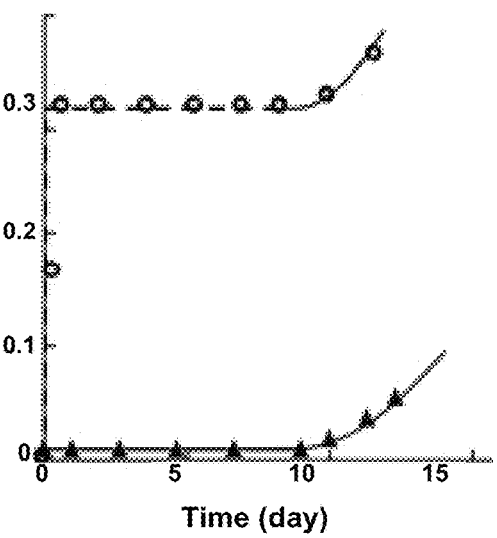

As the initial burst release commences, degradation of the polymer begins, increasing chain mobility and effectively leading to the formation of pores in the polymer matrix (FIG. 1, phase 2). Although a number of mechanisms have been proposed for this heterogeneous degradation profile, one hypothesis, which has been reinforced by experimental data, is based upon regions of varying amorphicity and crystallinity. It is believed that amorphous regions of polymer erode first, leaving behind pores (as shown using scanning electron microscopy). These pores appear to be essential for subsequent release (FIG. 1, phase 3).

With the cumulative growth and coalescence of these pores, agents are able to diffuse towards the surface of a polymer matrix that would otherwise be too dense to allow their passage (FIG. 1, phase 4). Thus, a pore is defined as a region of polymer matrix with an average molecular weight low enough to allow the release of encapsulated agent. (This is in contrast to the occlusion, which is defined as a region occupied by dissolved or solid agent, marked by the absence of polymer matrix.) Further, the molecular weight associated with release may vary for each encapsulated agent type (small molecule, peptide, protein, etc.), leading to a size-dependent restriction for agent egress.

With a size-dependent restriction on egress established, the degradation controlled release of any encapsulated agent can only occur when the following four conditions are satisfied. 1) The release agent must be present in the polymer matrix. 2) A pore must encompass the release agent. 3) That release agent must be able to diffuse through the encompassing pore. 4) The pore must grow and coalesce with others to create a pathway for diffusion to the surface.

The methods and compositions described herein are all applicable to a wide variety of active agents and polymer matrices.

The active agent may be a bioactive agent or a non-bioactive agent. The bioactive agent may be, for example, a therapeutic agent, a prophylactic agent, a diagnostic agent, an insecticide, a bactericide, a fungicide, a herbicide or similar agents. The non-bioactive agent may be, for example, a catalyst, a chemical reactant, or a color additive.

Illustrative bioactive agents include, but are not limited to, polynucleotides such as oligonucleotides, antisense constructs, siRNA, enzymatic RNA, and recombinant DNA constructs, including expression vectors.

In other preferred embodiments, bioactive agents include amino acids, peptides and proteins. By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

Examples of proteins encompassed within the definition herein include mammalian proteins, such as, e.g., growth hormone (GH), including human growth hormone, bovine growth hormone, and other members of the GH supergene family; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; alpha tumor necrosis factor, beta tumor necrosis factor; enkephalinase; RANTES (regulated on activation normally T-cell expressed and secreted); human macrophage inflammatory protein (MIP-1-alpha); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor-I and -II (IGF-I and IGF-II); des(1-3)-IGF-I (brain IGF-D; insulin-like growth factor binding proteins; CD proteins such as CD3, CD4, CD8, CD19 and CD20; osteoinductive factors; immunotoxins; a bone morphogenetic protein (BMP); T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

Further bioactive agents include smaller molecules, preferably for the delivery of pharmaceutically active agent, more preferably therapeutic small molecules. Suitable small molecule agents include contraceptive agents such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimethisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like.

Other active agents include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chloropromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; other steroids such as testosterone and testosterone propionate; sulfonamides; sympathomimetic agents; vaccines; vitamins and nutrients such as the essential amino acids, essential fats and the like; antimalarials such as 4-aminoquinolines, 8-aminoquinolines, pyrimethamine and the like; anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocomine methanesulfonate, dihydroergokrooyptine methanesulfate and combinations thereof; alkaloids such as atropine sulfate, Belladonna, hyoscine hydrobromide and the like; analgesics; narcotics such as codeine, dihydrocodienone, meperidine, morphine and the like; non-narcotics such as salicylates, aspirin, acetaminophen, d-propoxyphene and the like.

Further agents include antibiotics such as the cephalosporins, chlorarnphenical, gentamicin, kanamycin A, kanamycin B, the penicillins, ampicillin, streptomycin A, antimycin A, chloropamtheniol, metronidazole, oxytetracycline penicillin G, the tetracyclines, and the like. In preferred embodiments, the ability of the body's macrophages to inactivate pathogens is enhanced by the delivery of antibiotics, such as tetracycline, to the macrophages.

Additional agents include anti-cancer agents; anti-convulsants such as mephenyloin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins;

cytotoxic drugs such as thiotepa, chlorambucil, cyclophosphamide, melphalan, nitrogen mustard, methotrexate and the like.

The polymer matrix may be any polymer that is biodegradable. In certain embodiments, polymers that produce heterogeneous pores are especially useful. These pores ripen, connect, and produce pathways for release. Illustrative polymers include polyanhydrides, poly(α-hydroxy esters), poly(β-hydroxy esters), and poly(ortho esters). In preferred embodiments, the polymer includes poly(glycolic acid), poly(lactic acid), poly(lactide-co-glycolide), or a mixture thereof. Various commercially available poly(lactide-co-glycolide) materials (PLGA) may be used in the method of the present invention. For example, poly (d,1-lactic-co-glycolic acid) is commercially available from Alkermes, Inc. (Blue Ash, Ohio). A suitable product commercially available from Alkermes, Inc. is a 50:50 poly(d,1-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,1-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,1-PLA (Resomer® RG 206), and from Birmingham Polymers (Birmingham, Ala.). These copolymers are available in a wide range of molecular weights and ratios of lactic acid to glycolic acid.

The most preferred polymer for use in the practice of the invention is the copolymer, poly(d,1-lactide-co-glycolide). It is preferred that the molar ratio of lactide to glycolide in such a copolymer be in the range of from about 85:15 to about 50:50.

In certain embodiments, the compositions disclosed herein are modified-release medicaments. In particular, the compositions are sustained release compositions or medicaments that include at least two different populations of microparticles. Each individual microparticle may includes the active agent (or a combination of active agents) and at least one polymer matrix.

With this background in mind, the methods disclosed herein will be described in more detail below.

Methods:

Determining formulation specifications: A desired active agent (such as a drug or biomolecule) and dosing schedule is initially specified. Next, the selected agent's molecular weight, aqueous solubility and, if applicable, isoelectric point is determined from appropriate publications. Based on the molecular weight, the extent of degradation's effect on release will be assessed via the correlation set forth in FIG. 3A. If aqueous solubility is below ~2.5 mg/ml, then the limiting effects of dissolution must also be considered in predictions as described below in more detail. Finally, if the isoelectric point is above 8 then the active agent is assumed to bind to the polymer of the delivery vehicle and is therefore not yet amenable to design by our methods.

With appropriate agent properties and, in turn, mathematics defined as described below in more detail, predictions for the performance of multiple formulations are made, thus defining a library of building blocks. To focus this library, it is assumed that occlusion size (Rocc) is much less than particle size (Rp) thereby minimizing and initial release due to a formulation's internal morphology. This leaves only polymer lifespan or the mean time for pore formation (a function of polymer degradation rate (kCw) and molecular weight (Mwo) as per equation 5 below) as defining when release will occur. Thus a library of building blocks is computed from all physically possible or commercially attainable values of kCw and Mwo.

Next a recursive algorithm is employed to determine the optimal ratio (combination or mixture) of said building blocks for satisfying the specified release profile. An initial estimate of said combination is made by using a non-linear optimization to compute % composition of each formulation in the library based on a best fit (wSSE) with the initially specified release profile. This estimate is refined by removing from the library any formulation whose % composition is below 1% of the optimized mixture, on the basis that it is too small to work with on a bench-top scale. At this point a new optimization is run based on the refined library and the new wSSE will be compared to the prior value to determine if a significant loss of accuracy is predicted. (Significant deviation is defined as % change in wSSE>5%.) To save on material and labor costs successive optimizations are run each stepping up the limit for % composition by 1%. This cycle is terminated when wSSE shows a percent change of 5% or greater from its original value. The amounts of each component formulation specified by the algorithm upon completion define the simplest combination of building blocks that accurately satisfies the agent-dosing requirements.

In further detail, the algorithm involves the following steps:

Step 1: Compute performance of all formulations that can be made from commercially available polymers of specific class (e.g., PLGA copolymers) as described below in more detail. The list of polymers provides a matrix Mwo and kCw values. Values for Mwr are set by the agent choice (~4 kDa for most peptides and proteins).

Step 2: Run a non-linear optimization to determine the % total composition (or mass fraction) occupied by each formulation in a mixture optimized to best fits a desired profile (e.g., a constant rate of drug delivery for 1 month).

Step 3: Redefine the polymer list by eliminating the formulation(s) computed to have the lowest % composition in the mixture.

Step 4: Repeat steps 2 and 3 to refine/simplify the mixtures' composition until the iteration begins to produce significantly (% deviation=0.5% original prediction) less accurate results or until n=1. At this point the simplest possible mixture has been determined.

Manufacturing formulations that satisfy design criterion. Microparticle formulations may be fabricated using a standard emulsion-based solvent evaporation process or like technique (single emulsion, spray drying, solvent casting, extrusion, etc). To begin fabrication, the desired polymer is dissolved in dichloromethane, creating an "oil" phase. Then the desired amount of drug solution is be added by sonication to create an inner aqueous phase. This emulsion is poured into aqueous poly(vinyl alcohol) (PVA, which stabilizes the oil phase) and homogenized to establish an emulsion where "oil" droplets are suspended in a larger water phase. This emulsion is poured into an aqueous PVA reservoir and mixed for 3 hours. During this time, the dichloromethane solvent evaporates and the polymer-rich emulsion droplets precipitate into particulates. After precipitation, the microparticles are be collected by centrifugation and washed three times with deionized water. Once washed, the particles will be lyophilized for 48 hours and then frozen until use to maintain stability of the formulation. It will be appreciated that other techniques known in the art can be used to manufacture the sustained release compositions disclosed herein.

Methods: Microparticle Characterization. All microparticles will be characterized to confirm that model design specifications have been met. Microparticle size ($R_p$) will be determined using a volume impedance method, as described previously using at least 1,000 measurements. For the $R_{occ}$ measurement, microspheres prepared with a fluorescent conjugate form of ovalbumin will be imaged using confocal microscopy. Z-stacks will be compiled to ensure that the diameter of the occlusion is measured and not simply a cord. In addition to confocal microscopy, scanning electron microscopy (SEM) may also be used. For SEM analysis, microparticle cross sections will be prepared as done previously. Briefly, a small sample of microparticles may be freeze fractured via treatment with liquid nitrogen. Gold sputter coating may be applied for final imaging. For either microscopy technique, occlusion size may be determined by volume-averaged measurement of at least five randomly selected occlusions in three different frames.

Methods: Microparticle Loading. The average loading of the particles is required to normalize the cumulative release profile and determine correct dosing in experimental groups. To measure loading, a known quantity of particles is dissolved in DMSO and the resulting solution is mixed with a 0.5N NaOH solution containing 0.5 w/v % SDS. This new solution is allowed to stand for 1 hour, before being subjected to a detection assay. Specifically, the concentration of encapsulated, fluorescently-labeled agent is quantified with spectrophotometry. The loading is then calculated as the mass of agent per dry unit mass of particles.

Troubleshooting: Unexpected Results from Microparticle Fabrication. It is conceivable that altering the polymer molecular weight or encapsulated agent could affect microsphere properties such as size and/or loading. We are able to compensate for these variations without significantly altering our protocols. For example, if the volume average microparticle size is lower or higher than model predictions, filtration or centrifugation can be used to skew the particle distribution, effectively shifting the mean microsphere size. Further, if the occlusion size will lead to an initial burst that is too large, we can similarly enrich for larger particles, thereby decreasing the magnitude of the initial burst by reducing the ratio of $R_{occ}$ to $R_p$. Finally, if the loading of the particles is higher or lower than expected, we can increase or decrease the amount of microspheres used our in vivo release studies to ensure that the pre-specified dosing is accurately replicated. The present inventors have demonstrated that microspheres matching relevant model specifications can be fabricated. In all cases, the results of the fabrication process have been quite consistent, meeting model specifications in each attempt (based on a t-test using a 99% confidence interval).

Methods: In Vitro Controlled Release. Once characterized as meeting the physical parameters specified from the model predictions, the in vitro release from the fabricated microparticles may be studied to confirm that the formulations perform in accordance with the model release predictions. First, 15-20 mg of lyophilized particles is suspended in 1 mL of phosphate buffer solution. The suspension of particles is maintained by 20 rpm end-over-end mixing at 37° C. Measurements are taken every 8-14 hours during predicted burst periods and every 2-3 days during periods of sustained release by spectrophotometry of fluorescently labeled agent. The in vitro release behavior is documented for 3 different batches of particles manufactured in the same manner to gauge the reproducibility of the results. For comparisons of empirical release data to model predictions, determine $R^2$ values can be determined as done in other controlled release modeling studies. Importantly, $R^2$ values, being inherently dependent upon the mean of a dataset, are not as well suited for comparison of kinetic data. Thus, comparisons using weighted sum of square error and confidence intervals can also be implemented.

Troubleshooting: Unexpected Effects from Other Parameters. During validation, model predictions of controlled release largely matched experimental data by considering the five most influential parameters ($R_p$, $R_{occ}$, $kC_w$, $Mw_o$, $Mw_A$). In select cases, other less influential parameters (such as the loading or the osmolality) may also affect release, particularly when they are set at extreme values. For example, in a microsphere system where protein loading is set to be too high, 80-90% of the contents can be released in the initial burst. Conversely, if the osmolality of the internal aqueous phase is too high, then particle deformation can occur and no initial burst may be observed. From our experience, we can readily distinguish the signatures of these effects. Further, these specific effects are distinct from modeling issues stemming from the prediction of the mean induction time for pore formation, which would only be apparent much later in the release study. If either osmotic or loading effects are observed we can promptly correct them with a subsequent formulation, minimizing any setback in our experiments.

The method for determining formulation specifications is described below in more detail:

Agent concentration within a matrix (such a microsphere, rod, or thin film) can be calculated from Fick's second law (Equation 1) for any point in time (t) or space (r), provided that the agent is not generated or consumed in any reactions while within the matrix.

$$\frac{\partial C_A}{\partial t} = \nabla (D_{eff} \nabla C_A) \quad (1)$$

where $D_{eff}$ is an effective diffusivity term. Integrating $C_A/C_{Ao}$ over the entire matrix volume yields the cumulative fraction of agent retained in the matrix (P(t)) (Equation 2).

$$P(t) = V^{-1} \int C_A/C_{Ao} dV \quad (2)$$

In turn, the cumulative fraction of agent released (R(t)), a metric commonly used to document formulation performance, is simply (Equation 3):

$$R(t) = 1 - P(t) \quad (3)$$

At the center point, line, or plane of the matrix (r=0) symmetry conditions are defined such that $dC_A/dr=0$. At the matrix surface (r=$R_p$) perfect sink conditions are specified. A boundary also exists at a depth of $R_{occ}$ in from the matrix surface (r=$R_p$-$R_{occ}$) where continuity conditions are defined. In the subdomain from $R_p$ to $R_p$-$R_{occ}$ (terminating one occlusion radius in from the particle surface), agent is subject to the initial release, such that $D_{eff}$ is simply a constant (D), reflecting the movement of agent through the hydrated occlusions abutting the matrix surface. In the subdomain from 0 to $R_p$-$R_{occ}$, agent is subject to pore-dependent release, such that $D_{eff}=D\varepsilon$, where D is the diffusivity of the agent through the porous matrix and cis the matrix porosity.

For a system of like matrices, such as microspheres or sections in a thin film, that degrade randomly and heterogeneously, the accessible matrix porosity is simply a function of time as a discrete pore has, on average, an equal probability of forming at any position in the polymer matrix. Hence, the time until pore formation can be calculated from the degradation of the polymer matrix, as any differential volume containing a pore would have a lower average molecular weight than its initial value. Assuming that the polymer degradation rate is normally distributed, the induction time for pore formation will also follow a normal distribution. As this pore formation is cumulative, the time-dependent matrix porosity ($\varepsilon(t)$) can be described with a cumulative normal distribution function (Equation 4).

$$\varepsilon(t) = \frac{1}{2}\left[\text{erf}\left(\frac{t-\bar{\tau}}{\sqrt{2\sigma^2}}\right)+1\right] \quad (4)$$

In this equation, $\bar{\tau}$ is the mean time for pore formation and $\sigma^2$ is the variance in time required to form pores.

Implementation Calculating $\varepsilon(t)$. Calculating the cumulative normal induction time distribution ($\varepsilon(t)$) requires values for $\bar{\tau}$ and $\sigma^2$. For polymers that obey a first order degradation rate expression, the mean time for pore formation ($\bar{\tau}$) can be determined as follows:

$$\bar{\tau} = \frac{-1}{kC_w}\ln\left|\frac{M_{wr}}{M_{wo}}\right| \quad (5)$$

where $kC_w$ is the average pseudo-first order degradation rate constant for the given polymer type, $M_{wo}$ is the initial molecular weight of the polymer, and we define $M_{wr}$ as the average polymer molecular weight in a differential volume of matrix that permits the diffusion of the encapsulated agent. For blended polymer matrices, the value for $\bar{\tau}$ was calculated by averaging the results obtained from equation 5 for each component.

It is reasonable to believe that the matrix molecular weight at release ($M_{wr}$), which dictates how much degradation is required before release can occur, would vary depending on the size of the encapsulated agent. Macromolecules or larger agents can only diffuse through a section of matrix if it is almost entirely free of insoluble polymer chains. Hence the $M_{wr}$ for such agents is considered the polymer solubility molecular weight (668 Da for 50:50 PLGA as provided by Batycky et al.). As agent size decreases (as indicated by $M_{wA}$), however, egress can occur through more intact sections of polymer matrix (higher $M_{wr}$), as less free space is needed to allow their passage.

The distribution of polymer degradation rates ($kC_w(n)$) attributed to matrix crystallinity is needed to calculate the variance ($\sigma^2$) in the induction time distribution for pore formation ($\varepsilon(t)$). To determine $kC_w(n)$, the first order degradation rate equation $M_w = M_{wo}e^{-kC_w t}$ was linearly fitted at three different time periods to published degradation data for the desired hydrolysable polymer. Fitting the initial slope of the degradation profile provides the degradation rate constant of amorphous polymer as degradation occurs faster in amorphous regions of the matrix. Fitting data from the final weeks of degradation produces a rate constant for the crystalline material, as amorphous regions are largely eroded by this point. Finally, a fit of the entire degradation profile yielded a rate constant indicative of the overall morphology.

With values for $kC_w(n)$ defined, a distribution of induction times ($\tau(n)$) was calculated using equation 5. For blended polymer matrices this $\tau(n)$ includes values calculated at all component $kC_w(n)$ and $M_{wo}$. The standard deviation was taken for $\tau(n)$, then divided by a crystallinity-based factor and squared, yielding an adjusted variance ($\sigma^2$), which conforms with lamellar size data.

This crystallinity-based factor adjusts the probability of finding pores formed from the fastest degradation rate in $kC_w(n)$ to match the probability of finding a differential volume of matrix containing purely amorphous polymer. For all modeled cases, this differential volume is defined as a region large enough to allow the passage of a small virus or protein complex (20 nm diameter). As multiple lamellar stacks can fit into this differential volume, the probability that such a volume is purely amorphous can be calculated from of the number of stacks per differential volume and the average crystallinity of the matrix. From crystallinity data on 50:50 PLGA matrices, the probability of finding a purely amorphous differential volume is calculated as 0.05%. Thus, to ensure that the probability of finding a pore formed from the fastest degradation rate in $kC_w(n)$ also equals 0.05%, the standard deviation in the induction time distribution for pore formation was adjusted by a factor of 5. Similarly, factors of 4 and 2 were calculated from crystallinity data for 75:25 PLGA and polyanhydride matrices, respectively.

Solution and Regression

With values for $\bar{\tau}$ and $\sigma^2$ selected (defining $\varepsilon(t)$), a finite element solution to equation 1 was calculated (Comsol®, v3.3) for the given matrix geometry, using default solver settings. (To decrease computation time, the matrix geometry was simplified to one dimension based on symmetry, for a sphere, or high aspect ratio, for a thin film.) The resulting concentration profiles were numerically integrated to calculate the cumulative fraction of agent released (equations 2 and 3). For validation, the numerical solutions of the model were fit to experimental data sets by varying $M_{wr}$ and D. (It should be noted that data points charting the kinetics of the initial burst were omitted from these regressions, as the model only predicts the magnitude of this phase.) Each fit was optimized (Matlab®, R2007a) based on a minimized sum-squared error (SSE) or weighted sum-squared error (wSSE) when error bars were provided.

Validation

As derived above, values for D and $M_{wr}$, while not easily quantifiable, are needed to solve the fundamental model equations 1-5. Hence, to further develop the model, regressions to multiple data sets were conducted to relate these parameters to more readily attainable system properties. For these regressions, values for the readily attainable model parameters, $M_{wo}$ and $R_p$, were taken from the published data sets. $kC_w(n)$ was calculated and averaged from several different sources as described above. Data points documenting the kinetics of the initial burst were not included for fitting, as the model, in its current form, only predicts the magnitude of this phase. (This current limitation is described further in the Discussion section.) Properties for the experimental systems described by these regressions are listed in Table 1.

TABLE 1

List of experimental systems used for model validation

| Agent | $M_{wA}$/Da | Polymer | $M_{wo}$/kDa | $R_p$/μm |
|---|---|---|---|---|
| Metoclopramide | 297 | 50:50 PLGA | 98 | 75 |
| Ethacrynic ccid | 303 | 50:50 PLGA | 110 | 35 (film) |
| Betamethasone | 392 | 50:50 PLGA | 41.8 | 19.5 |
| Gentamicin | 477 | 50:50 PLGA | 13.5, 36.2 | 133, 276 |
| Leuprolide | 1 209 | 50:50 PLGA | 18, 30 | 20 |
| Melittin | 2 860 | 50:50 PLGA | 9.5 | 2.15, 3.5 |
| SPf66 | 4 700 | 50:50 PLGA | 100 | 0.6 |

TABLE 1-continued List of experimental systems used for model validation

| Agent | $M_{wA}$/Da | Polymer | $M_{wo}$/kDa | $R_p$/μm |
|---|---|---|---|---|
| Insulin | 5 808 | 50:50 PLGA | 6.6, 8 | 1.5 |
| Neurotrophic factor | 12 000 | 50:50 PLGA | 9.3 | 8.85 |
| BSA | 69 000 | PSA | 37 | 10 |

Predictions

To test the model, regression-free predictions were made for a variety of biodegradable matrix systems, each with published controlled release data. 16-18 Values for the parameters needed to make these predictions were all taken from the literature 16-18, 21, 35, 39-42 and, where applicable, translated through the correlations described above. The occlusion radius ($R_{occ}$) was found by averaging the sizes of 10 occlusions, randomly selected from scanning-electron or fluorescence microscopy images of the microspheres.

The model's predictive capabilities were explored by specifying a priori conditions such as occlusion ($R_{occ}$) and matrix ($R_p$) sizes as well as the mean polymer molecular initial weight ($M_{wo}$) and its distribution. Specifically, occlusion size was varied from that of a matrix with a homogeneously loaded, small molecule ($R_{occ}$<1 nm) to a larger occlusion containing drug (800 nm), as could be found in double emulsion formulation, $R_p$ was set between 8 and 150 μm and $M_{wo}$ was varied from 7.4 to 100 kDa. In addition, blends of common polyesters were considered such as a 2:1 ratio of 7.4 kDa 50:50 PLGA and 60 kDa PLA or a 1:1 ratio of 10 kDa and 100 kDa PLGA. To provide continuity all predictions were generated for a short peptide (900 Da) encapsulated in a spherical matrix.

Results

Validation

Figure 3A:
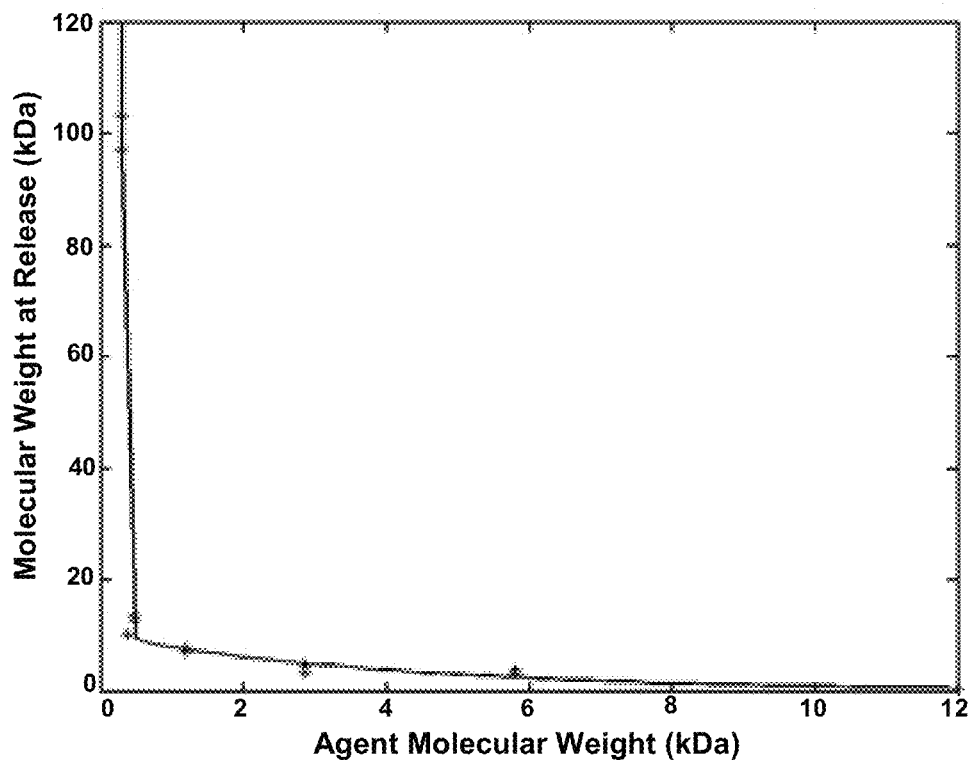
FIGS. 3A and 3B are graphs showing correlations for D and $M_{wr}$ developed from regressions to experimental data as referenced in Table 1. A) Plot of polymer molecular weight at the onset of drug release ($M_{wr}$) vs. release agent molecular weight ($M_{wA}$). The data used to form this correlation comes from 50:50 PLGA systems. B) Plot of D versus $R_p$. The line indicates the power expression, $D=2.071\times10^{-19} R_p^{2.275}$ which fits the estimations with an $R^2=0.95$.
Figure 3B:
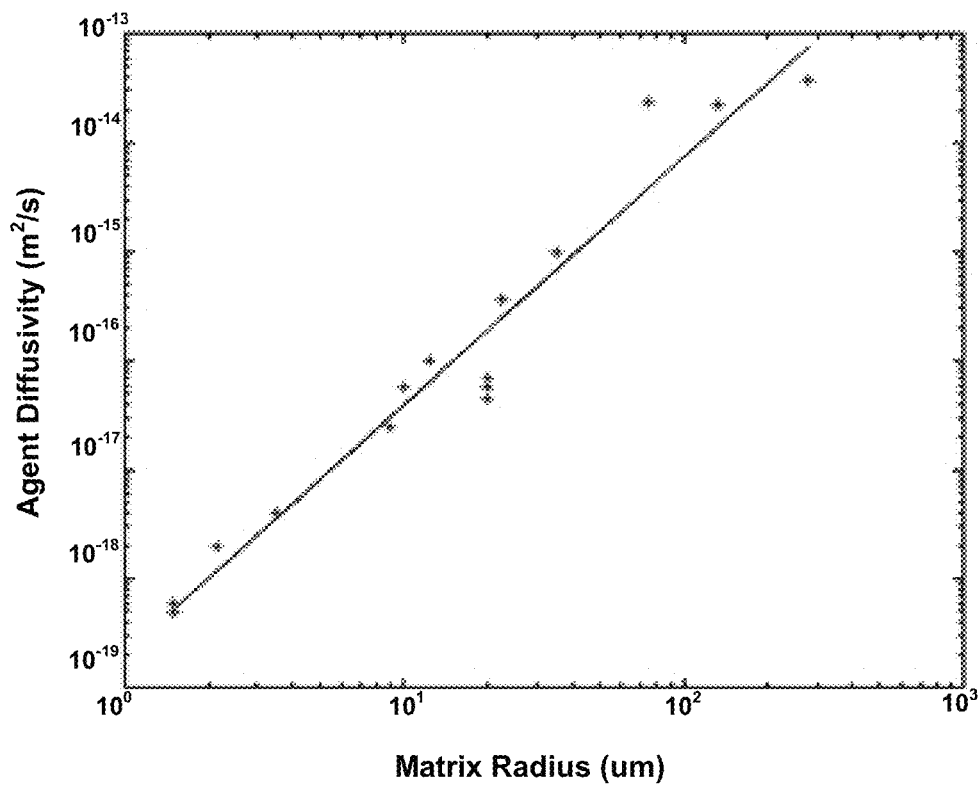

Solving the fundamental model equations requires values for D and $M_{wr}$, which are difficult to directly measure. Fitting the model to release data for a wide range of agents generated values for molecular weight of release ($M_{wr}$) that display a strong correlation with agent molecular weight ($M_{wA}$) as shown in FIG. 3A. Fitting a power expression ($y=ax^b$) to the plot of the regressed diffusivity values versus particle size data ($R_p$), as suggested by Sieppman et al., resulted in $a=2.071 \times 10^{-19}$ and $b=2.275$ ($R^2=0.95$) (FIG. 3B). These correlations compile data from multiple agents, polymer molecular weights and matrix sizes (Table 1).

Predictions of Release Data.

Figure 4A:
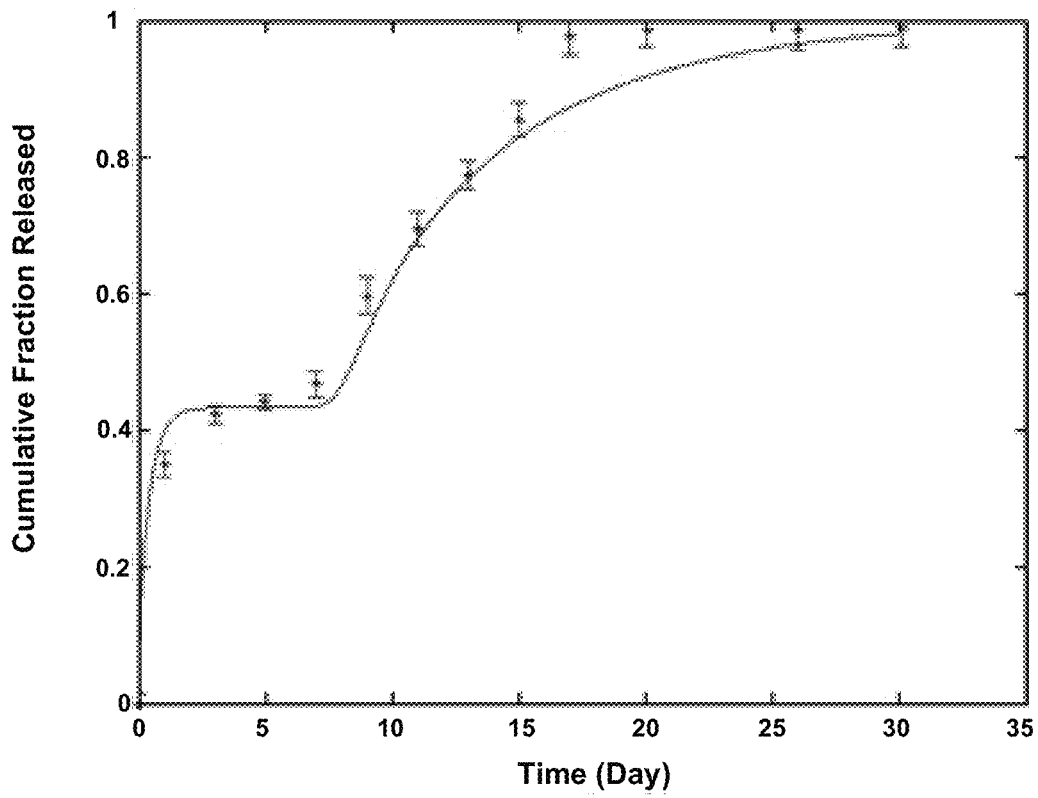
FIGS. 4A and 4B are graphs showing regression-free prediction for peptide release from PLGA microspheres. The $M_{wr}$ for melittin ($M_{wA}=2.86$ kDa) was calculated at 4.68 kDa from the correlation in FIG. 3A. A) For the 9.5 kDa 50:50 PLGA microsphere ($R_p=3.7$ μm, $R_{occ}=0.52$ μm) D was correlated at $4.06\times10^{-18}$ m²/s. B) The diffusivity (D) for 9.3 kDa 75:25 microspheres ($R_p=4.5$ μm, $R_{occ}=0.54$ μm) was calculated at $6.34\times10^{-18}$ m²/s.
Figure 4B:
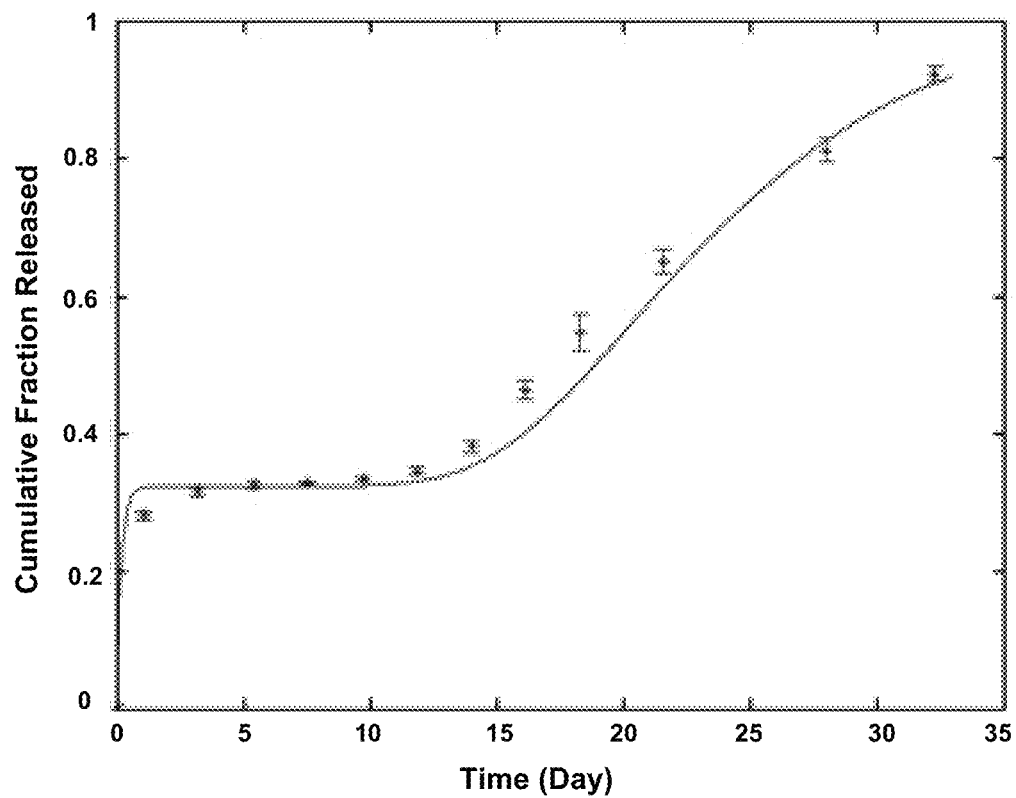
Figure 5:
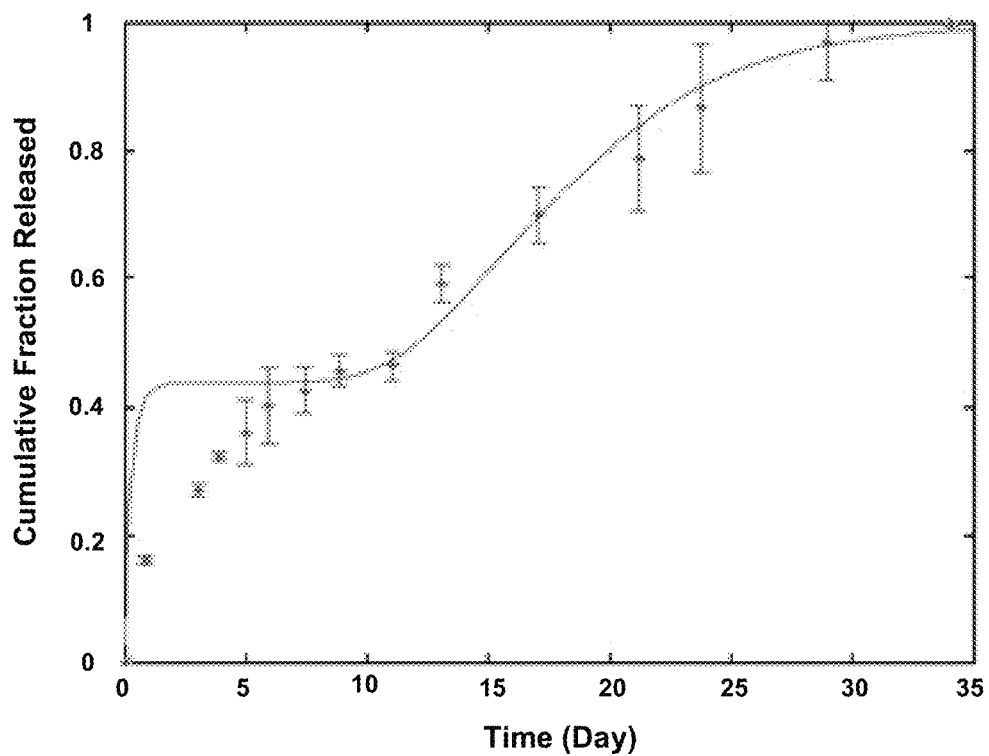
FIG. 5 is a graph showing a regression-free prediction for polyanhydride based microparticle release of BSA. System is composed of 20:80 CPH:SA polyanhydride ($M_{wo}$=18 kDa, $R_p$=10 µm and $R_{occ}$=1.54 µm). As the $M_{wr}$ values presented in FIG. 3A are specific to PLGA copolymers, the $M_{wr}$ for this prediction (940 Da) was acquired by fitting the model to data from microparticles fabricated in an identical manner using polysebacic acid (data not shown). In accordance with the correlation in FIG. 3B, D was set at 3.67× $10^{-17}$ m²/s.
Figure 6:
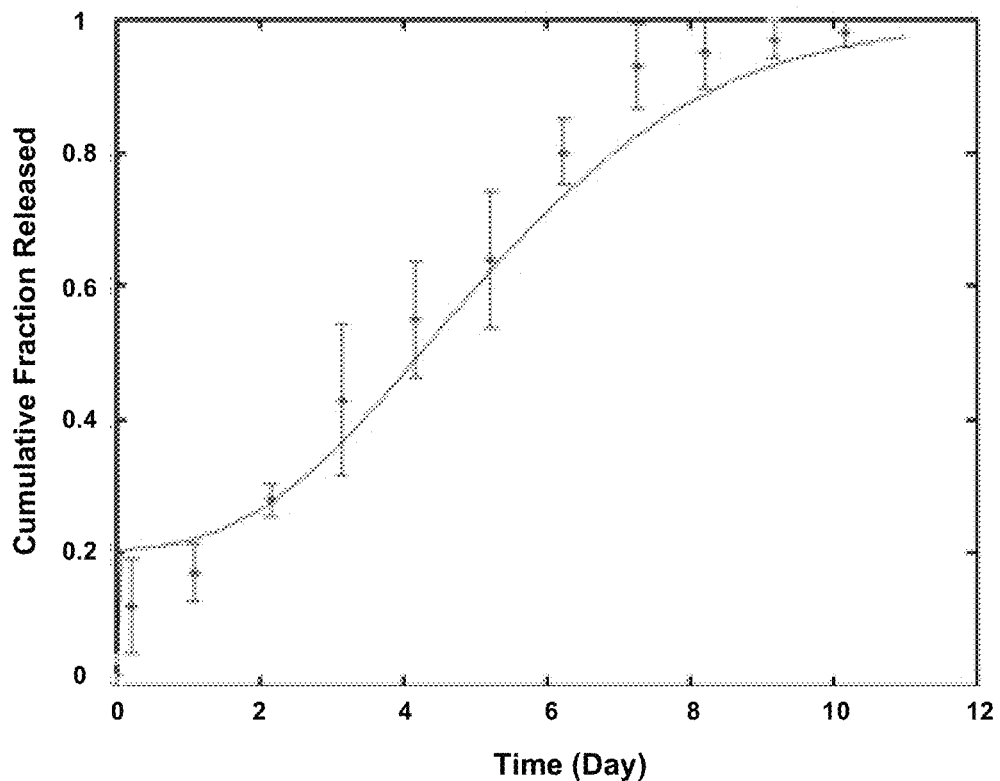
FIG. 6 is a graph showing regression-free predictions compared to small molecule release data from blended polymer microspheres. Gentamicin ($M_{wA}$=477 Da) was release from microspheres ($R_p$=374.6 µm and $R_{occ}$=24.7 µm) composed of a 1:1 blend of 13.5 and 36.2 kDa 50:50 PLGA (asterisks). As the $R_{occ}$ could not be determined from the published SEM images, the value of 24.7 µm was acquired from different sized gentamicin-loaded microspheres fabricated under like conditions. The $M_{wr}$ and D were correlated at 13.3 kDa and 1.48×$10^{-13}$ m²/s, respectively.

Regression-free model predictions for experimental data capture the magnitude of the initial burst, the duration of the lag phase, the onset of the secondary burst and the final release phase. FIG. 4 displays one set of predictions for peptide release from various PLGA copolymer microspheres. These predictions appear to extend to polymer matrices other than PLGA, such as polyanhydride microspheres (which, if sized less than 75 μm, are theorized to be entirely hydrated for the duration of release). The prediction for BSA release from 20:80 CPH:SA polyanhydride microspheres ($R_p=10$ μm) illustrates this broader applicability (FIG. 5). In addition, release predictions have also been made for matrices formulated from a blend of two different polymers (FIG. 6). All of these predictions serve to confirm that the model can describe: 1) the magnitude (but not the kinetics) of the initial burst from known occlusion size; 2) the duration of the lag phase from known polymer initial molecular weight, degradation rate and release agent molecular weight; 3) the onset of the initial burst from the matrix crystallinity derived rate distribution; and 4) the rate of subsequent release from the agent diffusivity (D) correlated to the matrix size.

Theoretical Predictions.

Figure 7:
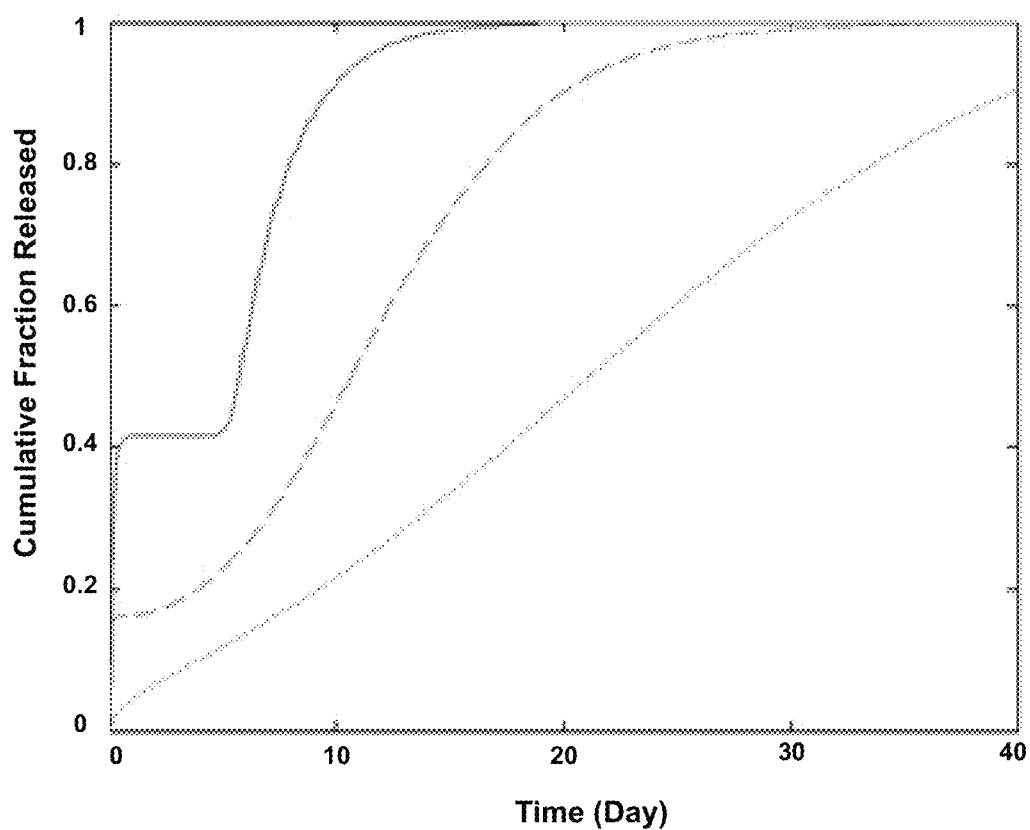
FIG. 7 is a graph showing theoretical release profiles for obtained by varying model parameters: $R_p$, $R_{occ}$, $M_{wo}$, and $kC_w(n)$. The profiles progress from a typical four phase release pattern (solid) to zero order release (dotted). For the solid line a 13 kDa 50:50 PLGA matrix was considered with $R_p$=150 µm, and $R_{occ}$=23.5 µm. The dashed line was generated based on a 1:1 blend of 10 kDa and 100 kDa 50:50 PLGA ($R_p$=20 µm, $R_{occ}$=1 µm) For the dotted line a 2:1 ratio of 7.4 kDa 50:50 PLGA and 60 kDa PLA was considered in a single emulsion matrix with $R_p$=8 µm.

By varying the readily attainable model parameters within logical bounds for controlled release formulations, it was possible to predict behaviors ranging from a four phase release profile to zero order release (FIG. 7). Changing the ratio of occlusion size ($R_{occ}$) to particle size ($R_p$) (representing the fraction of matrix volume defined as "near the surface") affected the magnitude of the initial burst (FIG. 2). The ratio of the polymer molecular weight at release (associated with the molecular weight of the release agent) to its initial molecular weight ($M_{wr}/M_{wo}$) and the mean reaction rate (associated with polymer type) were collectively found to be responsible for the duration of the lag phase. Lastly, modifying the distribution of degradation rates ($kC_w(n)$) or incorporating an $M_{wo}$ distribution (used to calculate the induction time distribution for pore growth) influenced the rate of onset for the secondary without affecting the initial burst. Tuning these parameters in combination can minimize the magnitude of the initial burst and the duration of the lag phase, while simultaneously slowing the rate of onset of the second burst, leading to a more linear release profile.

In the effort to hasten the development of biodegradable matrix-based, controlled release therapeutics, many models have been developed to describe the release of specific classes of agents, such as small molecules or proteins. In general, these models require parameters that can only be obtained by fitting controlled release data, or otherwise by carefully observing controlled release experiments. In order to eliminate the need for exploratory in vitro experiments, which investigate the drug dosing schedules supplied by potential controlled release therapeutics, a model must be able to predict, without regression, a broad range of release behaviors for a wide array of agents, entirely from tunable matrix properties. To meet this goal, we developed new methods of calculating the magnitude of the initial burst release and the duration of the subsequent lag phase, which allow these features to be predicted with commonly known parameters regardless of the encapsulated agent type, be it small molecule, peptide or protein. We also applied this model to numerous sets of published data to generate values for two correlations. These correlations complete a set of readily attainable parameters for making regression-free predictions of drug release from uniformly hydrated biodegradable matrices. Finally, by varying the tunable parameters over rational bounds, the range of potential release behaviors attainable with such systems were explored.

The comparison of model predictions and experimental data strongly suggests that the magnitude of the initial burst is directly proportional to the amount of agent localized to occlusions residing just inside the matrix surface. This region is defined over the entire surface of the matrix to a depth of $R_p-R_{occ}$, such that any occlusion localized to this region would abut the matrix-reservoir interface. Prior models attributing the initial burst to the amount of agent adsorbed to the matrix surface required the fitting of empirical parameters for each new absorption/desorption drug type. Further, results from several studies examining release from particles of uniform size and surface morphology, but varying occlusion size (based on the formulation method), suggest that it is unlikely that desorption from the surface (with surface area being proportional to the magnitude of the initial burst) is responsible for the initial burst phase of release.

Regression-free predictions of published experimental data also suggest that the model consistently calculates the duration of the lag phase for release agents ranging from small molecules to proteins. Prior models have only accurately predicted the duration of the lag phase for either small molecules or proteins. The current model establishes a polymer molecular weight associated with release ($M_{wr}$) and inversely correlates it to agent molecular weight ($M_{wA}$) (FIG. 3A). The concept that small molecules can diffuse more readily through a higher molecular weight polymer matrix than larger molecules is supported by both diffusion flow cell studies and careful analysis of release data. In addition, scanning electron microscopy and other morphological studies have shown that with degradation, PLGA matrices become increasingly porous solids. The current model attributes this heterogeneous degradation to matrix crystallinity, a mechanism also supported by previous models.

The model predicts the onset of the secondary burst (FIG. 1) using expressions that have both similarities and fundamental differences with those presented in the literature. Like prior models, the current work employs Fick's second law with an $D_{eff}$ dependent on matrix porosity. Saltzman and Langer first derived this expression to predict protein release from non-degradable porous polymers. Their lattice-based percolation calculations yield an accessible porosity that fits a cumulative normal distribution, a feature that our model is able to implement without estimated parameters. Recent controlled release models based on stochastic methods have also successfully employed a version of this equation to describe the egress of small molecules from regressed degradation rate constants. The current work is, however, fundamentally different from these prior models as it describes pore formation in biodegradable matrices entirely from known parameters and applies to a broad range of agents, including small molecules, peptides, and proteins.

As mentioned in the Results section, the diffusivity values calculated for FIG. 3B are consistent with those found in the literature. These diffusivities display a power dependence on the size of the encapsulating matrix, where $D=aR_p^b$. This expression was originally developed by Siepmann et al. to compensate for the size-dependent increase in degradation rate that occurs in autocatalytic polymers such as PLGA. Further, even though this power expression was only validated for lidocane release from 45 kDa PLGA microspheres, we demonstrate that it applies nearly as well to the much broader range of matrix sizes, polymer molecular weights, and agent types examined herein (FIG. 3B, Table 1). The diffusivity coefficients ranging from $10^{-14}$ to $10^{-16}$ m$^2$/s calculated in prior models also support this finding. Our regression-free predictions (FIG. 4-6) help to confirm that this power expression will relate D to matrix size for many different polymers with an acid-based, autocatalytic, first-order rate expressions, including both polyesters and polyanhydrides.

Finally, having confirmed the model's predictive capabilities, the range of release behaviors that can potentially be attained from bulk eroding matrices were explored. Predictions for such matrices cover a continuum of behaviors ranging from abrupt burst-lag-burst profiles to sustained linear release (FIG. 7). These profiles satisfy the dosing schedules for numerous therapeutic applications, such as the constant delivery of a chemotherapy agent or the replication of multiple vaccine doses with a single injection. Along with (1) the model's applicability to a wide array of agents and (2) its use of physically relevant parameters, its ability to capture a broad range of release behaviors (3) completes the set of three specifications required for any framework that supports a rational design methodology.

Also described herein is the first model suitable for predicting a broad array of release behaviors not only from bulk eroding systems, but also surface eroding matrices and those that transition from a surface eroding to a bulk eroding degradation scheme during the course of degradation. Specifically, the current model combines diffusion/reaction equations, which account for the system's hydration kinetics, along with sequential descriptions of dissolution and pore formation to compute drug release. Further, all parameters required to solve these equations can be obtained prior to controlled release experiments, allowing predictions to be made without regression. In support of prior work reporting empirically obtained critical lengths 2, the diffusion/reaction equations employed by the current model are used to compute this characteristic parameter from rate expressions. To test the model's accuracy, regression-free predictions were compared with published controlled release data from several different polyanhydride and poly(ortho ester) implants.

Methods

Release Paradigm

Consider a hydrolysable polymer matrix loaded with a finite amount of release agent or drug. This agent is randomly dispersed throughout the matrix in a powdered or crystalline form. Further the agent is loaded discretely (below its percolation threshold), occupying either small granules or larger occlusions, as dictated by the matrix fabrication method. These occlusions or granules are distributed randomly throughout the polymer matrix, such that the probability of finding drug at any point in the polymer matrix is constant at all positions within the matrix.

At time zero, water or buffer begins to hydrate the matrix. Specifically, water diffuses into the matrix and is simultaneously consumed through the hydrolysis of the polymer matrix. Hence, a larger matrix with a faster hydrolysis rate, such as a polyanhydride implant, will have a sharper concentration gradient of water than a smaller matrix (microsphere) or one with a less labile polymer, such as a poly (lactic-co-glycolic) acid.

Following the hydration of a region of matrix, release of drug can be limited by its solubility or dissolution kinetics. The dissolution rate expression for this process depends upon the agent's solubility and concentration as well as the concentration of solvent. If an agent is highly soluble in water, dissolution may happen on a time scale that is much shorter than the duration of release. In systems where hydrophobic molecules have been encapsulated, however, dissolution can occur over a considerable amount of time, dramatically affecting the release profile.

After an agent has dissolved, its diffusive egress may be further restricted by the encapsulating matrix. In this case, the matrix needs to degrade to the point where a network of pores is formed, permitting egress of encapsulated agent. This degradation is assumed to happen randomly and heterogeneously throughout hydrated regions of the matrix. Further, the degradation of the matrix occurs in tandem with the dissolution of the agent, and both are dependent upon the hydration kinetics of the system. The interplay between these factors can be translated into a framework of coupled equations for describing release.

Model Development

The time-dependent concentration profile of water within a hydrolysable polymer matrix of initial molecular weight ($Mw_o$) can be calculated from competing diffusion-reaction equations. As water diffuses into a matrix, a process described by Fick's second law, it is also consumed in hydrolysis of the polymer matrix, (written below as a second order reaction, which applies to both polyesters and polyanhydrides). Hence, equation 6 below describes the presence of water within the polymer matrix.

$$\frac{\partial C_W}{\partial t} = \nabla(D_W \nabla C_W) - k C_w M w \tag{6}$$

Where $C_W$ is the time dependant concentration of water, $D_W$ is the diffusivity of water in the polymer matrix (found to be on the order of $10^{-12}$ m$^2$/s for a broad array of systems[22]), k is the degradation rate constant, and Mw is the polymer molecular weight.

As part of the hydrolysis reaction, polymer bonds are also broken leading to a decrease in the molecular weight of the polymer matrix. The kinetics of this process can be described by the standard second order rate expression commonly used for both polyesters and polyanhydrides. (Equation 7)

$$\frac{\partial M w}{\partial t} = -k C_w M w \tag{7}$$

It is assumed that components of the polymer matrix (e.g. initially high molecular weight polymer degradation products) do not diffuse considerably before the onset of erosion (Mw≈4 kDa), by which time the release of most types of agents will have commenced. In line with previous models, a "degradation front" can be defined at a point in the polymer matrix where the gradient of the polymer molecular weight (dMw/dr vs. r) is at a minimum. This minimum is defined as the inflection point of the continuous function, Mw(r), such that the initial average molecular weight at this front is ½ Mw$_o$, provided that the core of polymer matrix is still at its initial molecular weight.

With the hydration kinetics defined, the dissolution of the drug can be calculated, which is normally done with a second order rate expression. Unlike the standard systems used to derive this second order expression, the solvent concentration of the present system varies with position and time, and hence must be considered as well. The standard expression is also written in terms of the solute surface area and mass transfer coefficient which have been translated into equivalent, readily measurable parameters. (Equation 8)

$$\frac{\partial C_S}{\partial t} = -k_{dis} C_{Sn} C_{An} C_{Wn} \tag{8}$$

where $k_{dis}$ is the intrinsic dissolution rate constant, $C_{Sn}$ is the normalized concentration of solid drug in the polymer matrix, $C_{As}$ is the difference between the aqueous agent concentration and its maximum solubility ($C_{Amx}$), normalized by $C_{Amx}$, and $C_{Wn}$ is the normalized concentration of water. Next, the position-(r) and time-(t) dependant concentration of dissolved agent in a polymer matrix can be calculated from Fick's second law and the dissolution rate expression. (Equation 9)

$$\frac{\partial C_A}{\partial t} = \nabla(D_{eff} \nabla C_A) + k_{dis} C_{Sn} C_{An} C_{Wn} \tag{9}$$

where $D_{eff}$ is an effective diffusivity term. Integrating the total normalized concentration of agent in the matrix over all space yields the cumulative fraction of agent remaining in the matrix at each point in time. (Equation 10)

$$P(t) = V^{-1} \int \frac{C_S + C_A}{C_{So}} dV \tag{10}$$

In turn, the cumulative fraction of agent release (R(t)), a metric commonly used to document formulation performance, is simply: (Equation 11)

$$R(t) = 1 - P(t) \tag{11}$$

The $D_{eff}$ term in Equation 9 is dependent on the matrix porosity (ε) and the diffusivity of the agent through the porous matrix ($D_A$). ($D_{eff} = D_A \varepsilon$) The time- and space-dependant matrix porosity follows a cumulative normal distribution function, based a molecular weight or degradation rate distribution of the given polymer. (Equation 12)

$$\varepsilon = 1 - \frac{1}{2}\left[\text{erf}\left(\frac{Mw - Mw_r}{\sqrt{2\sigma^2}}\right) + 1\right] \tag{12}$$

The variance ($\sigma^2$) is based on the crystallinity of the polymer matrix and corresponding distribution of degradation rates, as done previously. The molecular weight of the polymer matrix during release (Mw$_r$) has been previously correlated to the molecular weight of the agent for common biodegradable systems. The diffusivity ($D_A$) of agents passing through the newly-formed pores in the polymer matrix has been correlated to bulk eroding matrix size. This correlation is based on the idea that a larger matrix will experience more rapid degradation due to autocatalysis than a smaller one and therefore have more highly developed pores, allowing the less restricted passage of agent. For a surface eroding matrix, autocatalytic degradation only occurs in the region of matrix that is hydrated, thus the system's critical length is used to determine the diffusivity from published correlations.

The boundary conditions for the polymer phase, as well as the aqueous and solid release agent phases, match those defined in a prior model for bulk eroding matrices. Briefly, symmetry conditions (dC$_n$/dr=0) are defined at the matrix center and perfect sink conditions (C$_n$=0) are set at the matrix surface (at radius R$_p$ and length L in a cylinder or disk). For water concentration, the same internal symmetry conditions still apply, but the concentration of water at the matrix surface is set to match that of an infinite reservoir, with a concentration of Cw$_o$ calculated as the density of water over its molecular weight. Further, when the encapsulated agent is gathered in large occlusions or pockets (relative to the size of the entire matrix), such as would be found in a double emulsion fabricated microsphere, the matrix should be represented with two sub-domains, as demonstrated previously, to account for the resulting initial burst.

Limiting Cases

Depending on the nature of the encapsulated agent, it may be possible to simplify the mathematical description of release. If an agent possesses a high aqueous solubility and dissolves rapidly, such that the rate of dissolution is at least 2 orders of magnitude faster than the rate of diffusion, the timescale of dissolution is negligible. When modeling such cases, the drug was assumed to dissolve instantaneously in water. Hence, Equation 8 can be neglected entirely and Equation 9 can be simplified to the following form. (Equation 13)

$$\frac{\partial C_A}{\partial t} = \nabla(D_{eff}\nabla C_A) \quad (13)$$

where $C_{Ao}$ becomes the initial concentration of agent. In total, these simplifications reduced the model to three sets of diffusion-reaction equations instead of four and eliminated three input parameters ($C_{So}$, $k_{dis}$ and $C_{Amx}$).

Alternatively if an agent has a $Mw_r>Mw_o$, by definition, it can diffuse freely through the newly hydrated polymer matrix and does not require degradation of the matrix for egress. Specifically, the agent is small enough to pass freely through the matrix and, as such, pores formed during degradation are no longer needed to provide a pathway for diffusive egress; hence $D_{eff}=D_A$. In this case the expression for matrix porosity (Equation 12) can be neglected.

Model Implementation

By adopting the proven approach to calculating release as detailed in section 2.2, existing correlations can be used along with the model to generate regression-free predictions. To calculate such predictions, the model was coded in Matlab® (Mathworks, r2007a) and computed using the finite element method on Comsol® (v3.1). Meshing was successively refined, until node-density independent results were observed. Otherwise, default solver settings were maintained.

Critical Length

To investigate the effects of polymer molecular weight ($Mw_o$) and degradation rate (k) on the transition from surface to bulk erosion, only equations 11 and 12 were considered. This transition occurs at a set matrix size, dubbed the critical length. Burkersroda et al originally defined the critical length as the distance water can travel through a matrix before the rate of diffusion equals the rate of degradation, such that in a surface eroding system, the rate of degradation surpasses the rate of diffusion. However, when mathematically accounting for these two rates with Fick's second law and a second order rate expression (applicable to autocatalytic hydrolysable polymers) this original definition becomes physically untenable because the $C_w$ term in the hydrolysis rate expression prevents the reaction rate from ever surpassing the diffusion rate. Thus, in order to determine the erosion mechanism of the matrices examined here in, we defined critical length as the matrix size where the polymer residing in the degradation front hydrolyzes at its most rapid rate, as noted by a minimum in $dMw_f/dt$ vs. t. In other words, during surface erosion, this front moves progressively inward, slowing its traverse only as the matrix begins to uniformly hydrate. With the onset of bulk erosion, the hydrolysis reaction taking place throughout the matrix can no longer consume the water before it penetrates to the matrix core. This leads to a matrix where the water concentration is at a maximum and the polymer molecular weight has not significantly decreased from its initial value. Together, these conditions maximize the degradation rate ($-kC_wMw$), resulting in the fastest possible drop in the average polymer molecular weight. Hence, it can be said that the matrix size, where degradation proceeds (on average) at its fastest average rate, denotes the end of surface erosion and the onset of bulk erosion, and therefore can be defined as the critical length.

Using this definition, the critical length was calculated for a variety of polymers, including PLA, PLGA, PFAD:SA, and PSA, at initial molecular weights ranging from 5 kDa to 130 kDa. The results of these calculations were used to determine if published release data was generated by surface eroding, bulk eroding, or transitioning phenomena. Specific calculations were also performed to check the erosion mechanism of matrices used in other modeling literature.

Release Predictions

The simplified forms of the model described in section 2.2.1 were validated against release data from matrices that could be represented in 2-dimensions using axial symmetry. Values for common model parameters $R_p$, L (for a cylinder), $Mw_o$, $Mw_A$, $C_{Wo}$, $C_{So}$, $C_{Amx}$, k, $D_w$, and $k_{dis}$ were specified directly from, or calculated using parameters specified in, the materials and methods sections of published literature. Existing correlations were used to calculate values for $D_A$ and $Mw_r$ using formulation parameters that would be available prior to controlled release experimentation.

It is important to note that the poly(ortho ester) matrices investigated herein are unique in the field of controlled release because they contain a small molecule anhydride excipient. This is proposed to alter the degradation mechanism of the polymer by increasing the rate of autocatalysis in the system. Fortunately, data on the hydrolysis of this anhydride excipient was published for these matrices and was used to enhance model calculations. Specifically, this data was used to calculate the amount of water diverted from polymer degradation into anhydride hydrolysis as a function of time. The newly calculated rate expression was amended to the hydrolysis reactions to adjust for the additional consumption of water by the excipient.

Results

Matrix Degradation Kinetics

Figure 8A:
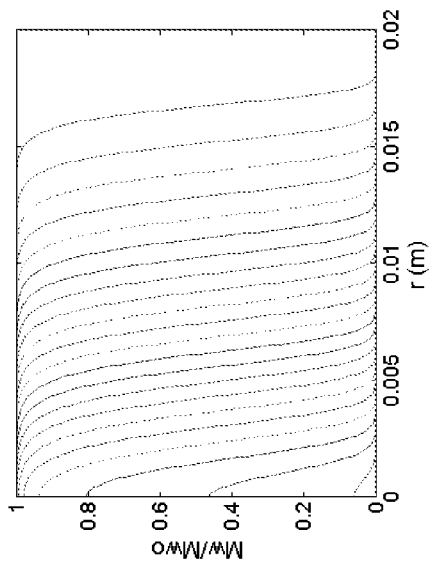
FIGS. 8A-8C are graphs depicting degradation profiles (Mw relative to $Mw_o$ as a function of distance and time) for various spherical matrices of 10 kDa PSA. Matrix size is varied (X axis) to explore the various erosion schemes.
Figure 8B:
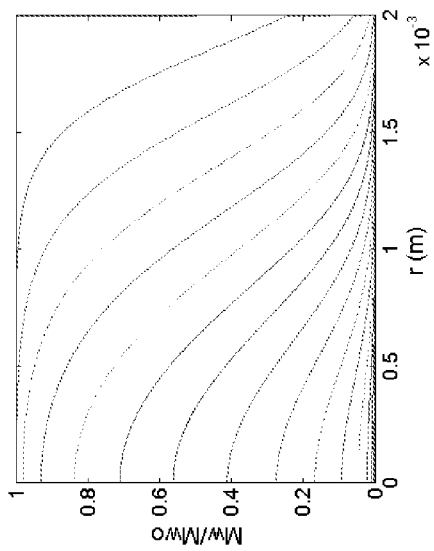
Figure 8C:
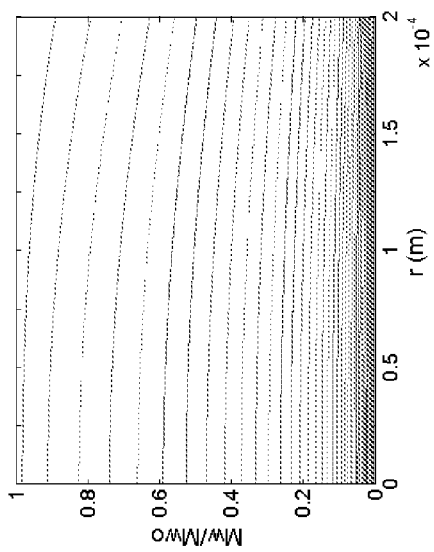

Solutions to equations 6 and 7 generate hydration and degradation profiles for a specified polymer matrix. FIG. 8 shows degradation profiles ($Mw/Mw_o$ as a function of r and t) for matrices composed of a single polymer where the dominate erosion mechanism has clearly been predetermined by carefully selecting the matrix size. In a system undergoing surface erosion, the degradation-erosion front will move inward toward the center of the matrix as both degradation and erosion are confined to the periphery. (FIG. 8A) In bulk eroding systems, in which degradation occurs randomly throughout the matrix, the matrix size remains constant as its average molecular weight decreases. (FIG. 8C) This change in average molecular weight begins at the most rapid rate possible, with water concentration and polymer initial molecular weight both being at maximal values, and decreases as the number of hydrolysable bonds is depleted. Hence, average degradation rate in the polymer matrix should be at a maximum with the onset of bulk erosion (or in other words, during a transition from surface to bulk erosion). (FIG. 9 A) In turn, the critical length is calculated as the matrix size (marked at the center of the degradation front) when this transition occurs. Increasing the polymer degradation rate, indicating a more labile hydrolysable bond type, correspondingly decreases the critical length, indicating more dominate surface eroding behavior. Likewise, increasing the polymer initial molecular weight also decreases the critical length. (FIG. 9 B)

Having determined the matrix specifications required to maintain surface erosion, the model's ability to predict controlled release from matrices with a variety of different erosion mechanisms was examined. Further, systems with different hypothesized, release rate-limiting steps were also examined. The tested systems range from bupivacaine release from FAD:SA polyanhydride disks (dissolution limited, bulk eroding), to gentamicin release from FAD:SA polyanhydride rods (degradation limited, surface eroding), to amaranth release from POE disks (degradation limited, surface and bulk eroding).

Dissolution Controlled Release

Work by Park et al. examines the release of a small molecule, bupivacaine, from a 50:50 FAD:SA polyanhydride disk with a 4 mm radius and 1 mm thickness sized at slightly below the calculated critical length for this system (~1.7 mm). This suggests that the system would exhibit bulk eroding behavior and, as such, model predictions made with and without taking into account the hydration kinetics should both match the bupivacaine release data with comparable accuracy. (FIG. 10) In line with this result, both predictions matched the data within acceptable bounds, with the prediction from the full model producing a slightly more accurate result than the simplified version of the model that neglected hydration kinetics. It was also hypothesized that dissolution kinetics were an important factor in determining the release rate of bupivacaine and failing to consider them increased the SSE by a factor of 25 (SSE=4.9004, data not shown).

Degradation Controlled Release

Figure 11:
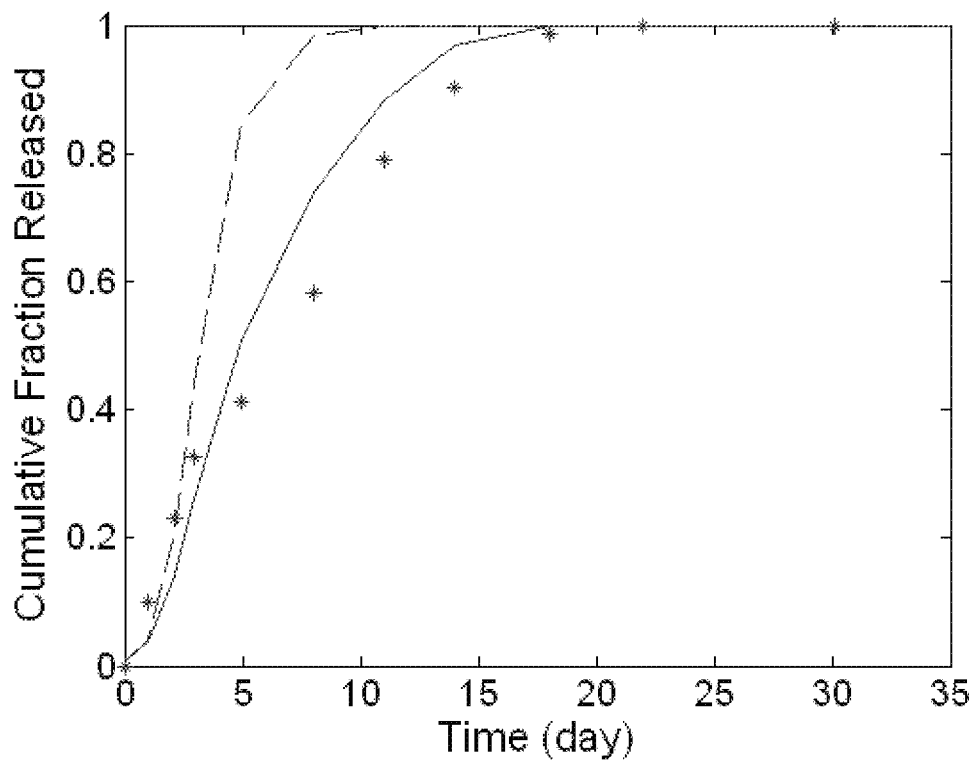
FIG. 11 is a graph showing predictions for degradation-controlled release of drug. The experimental data (asterisks) charts gentamicin release from FAD:SA matrix rods. Model predictions were generated without regression while considering surface erosion (solid, SSE=0.0657) and assuming bulk erosion (dashed, SSE=0.4350). To generate these regression-free predictions, the following values were used: $R_p$=2 mm, L=12 mm, $Mw_o$=35.8 kDa, $Mw_r$=13.3 kDa, $D_A$=5.94×$10^{-12}$ m²/s.
Figure 13:
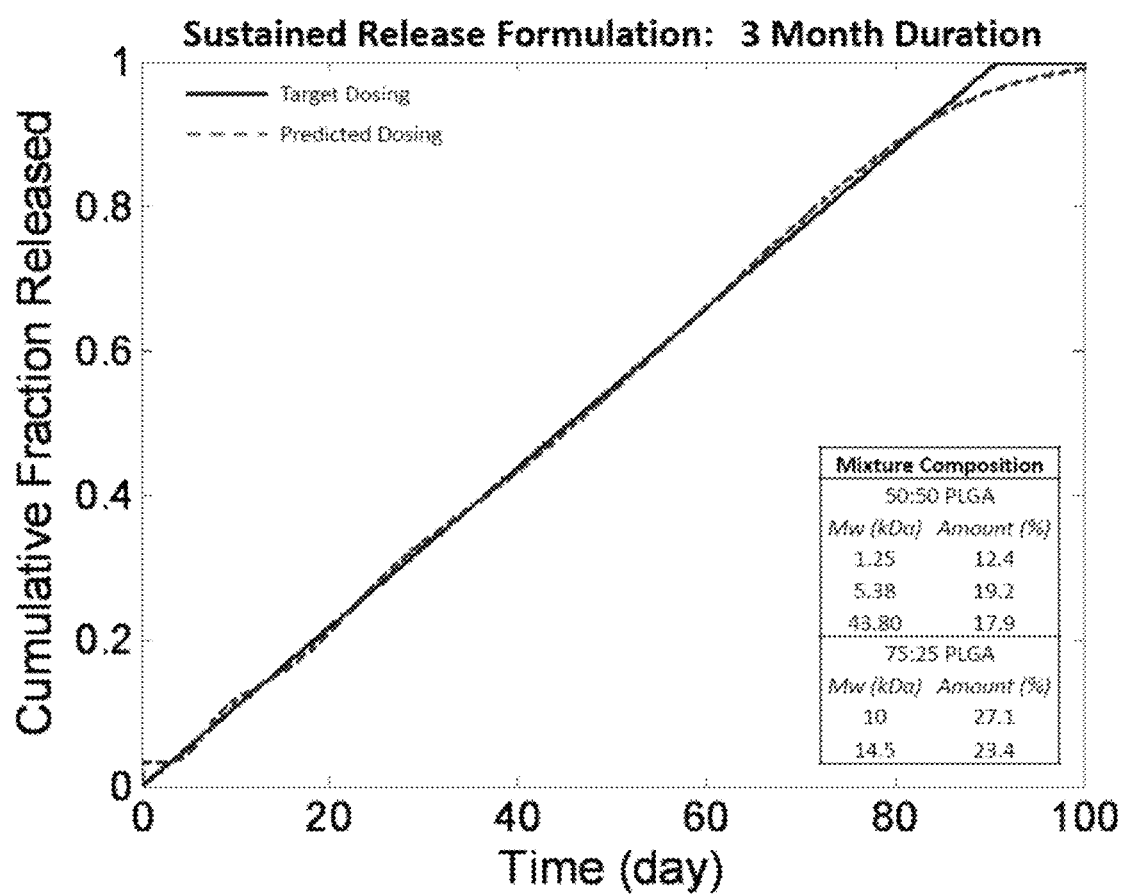
FIGS. 13-15 are graphs depicting model sustained release formulations and their predicted release rates.
Figure 14:
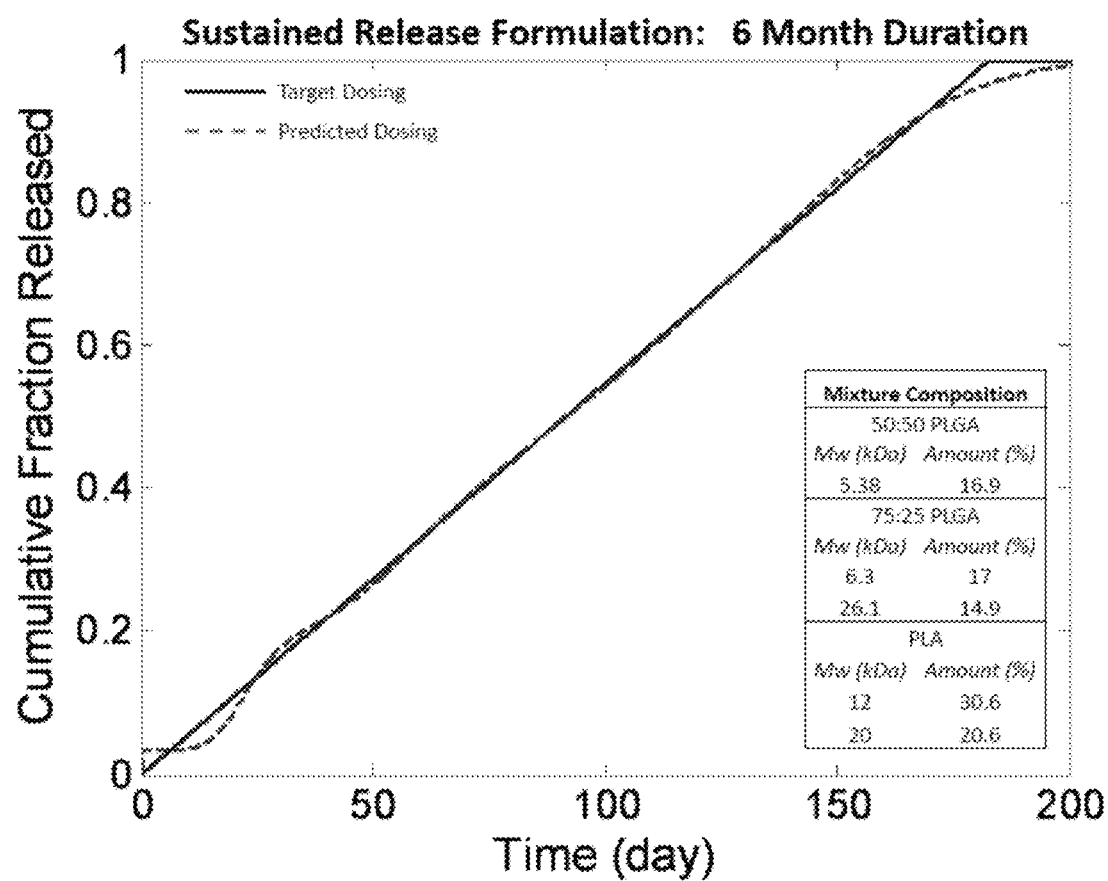

Stephens et al documented gentamicin release from a 35.8 kDa $Mw_o$ 50:50 FAD:SA polyanhydride bead with a 4 mm diameter and a 12 mm length, a matrix on the same order of magnitude as, but still slightly larger than the calculated critical length of 1.9 mm. Based on the calculations of critical length presented in FIG. 9B and the those made by Burkersroda et al., this system should exhibit surface eroding behavior, and any attempt to accurately model it should account for hydration kinetics. If a prediction for release is made without accounting for hydration kinetics, as detailed in, a relatively poor fit to the data is observed (SSE=0.4350). However, when accounting for hydration kinetics, using equations 1 and 2, the model's prediction improved dramatically (as expected), resulting in an SSE of 0.0657. (FIG. 11)

Work by Joshi et al examined amaranth dye release from POE disks (10 mm diameter, 1.4 mm thick), which had their erosion mechanism controlled by the addition of phthalic anhydride. When a low amount of anhydride (0.25 w/w %) was present in the disk, a bulk eroding mechanism was postulated to dominate, a point confirmed by our own critical length calculations (data not shown). In contrast, with the addition of just 1% anhydride excipient, the critical length dropped to 684 μm, a value slightly below the shortest matrix dimension, suggesting that surface erosion should dominate (at least at early times). Predictions of drug release from both of these systems take into account both the increase degradation rate from and the consumption of water by the anhydride excipient. If these factors are not considered increased error is observed in the predictions. (data not shown) Accounting for these effects significantly improved prediction for both the 0.25% anhydride matrix, reducing error by a factor of 4, and the 1% anhydride matrix, reducing error by a factor of 6, when compared to previously published results.

DISCUSSION

Biodegradable matrices for controlled release have been traditionally classified as either surface or bulk eroding and mathematical models of drug delivery from these systems have often reflected this classification in their assumptions. Recent data suggests that many surface eroding systems actually transition to a bulk eroding mechanism while drug release is occurring. With this in mind, a new model was developed to predict drug release from matrices undergoing multiple different erosion schemes, the first of its kind to describe the release of a wide array of agents without regression. This model uses diffusion-reaction equations to describe the hydration kinetics, drug dissolution and degradation controlled release. Using the equations governing matrix hydration, a mechanistically accurate method for calculating a system's critical length was developed, and then applied to a range of common systems. Regression-free predictions (which use parameters that can be obtained prior to release experimentation) were made including and (for validation purposes) ignoring the effects of matrix hydration in both smaller and larger than their respective critical lengths. Specifically, the model has been used here to predict bupivacaine release from polyanhydride disks and gentamicin release from polyanhydride cylinders as well as amaranth red release from poly(ortho ester) disks. The model's applicability is not, as shown previously, limited to small molecules and should apply with comparable accuracy to systems that encapsulate and release macromolecules.

Several of the fundamental concepts from the current model's paradigm have been separately employed in prior models. However, the equations used to translate these concepts into mathematical predictions for drug release have, however, been altered in some way from their previous forms. For example, a dissolution rate expression has been used in prior published work. Unlike this previously published expression, the form in equations 3 and 4 include a term for the dimensionless concentration of water that accounts for potential solubility limitations associated with partially hydrated systems. Another example comes from the porosity expression, which has been translated from a time-dependant form that assumes a uniform degradation rate to a version with broader applicability, based on the local molecular weight of the polymer matrix. Finally, the concept of using diffusion/reaction equations to create a model that uniformly captures different erosion schemes has also been investigated before. One prior model based on species-dependant, diffusion/reaction equations was successfully developed and applied to data for dye release from POE disks (FIG. 12). The results from predictions in that work are compared to results from our more comprehensive model below. Importantly, predictions using this previous model required system-specific parameters that could not be directly measured in order to generate predictions. In the current model, predictions have been simplified using widely tested mathematical descriptions of pore-mediated release and polymer degradation. It is important to note that these simplifications have not hindered the current model's predictive power. For instance, regression-free predictions from the current model describe the amaranth red release data used to validate this prior work, with a greater degree accuracy (i.e. lower error in the prediction of data).

An examination of hydration and degradation profiles based on Equations 6 and 7 show that the current model can produce profiles that resemble surface erosion, bulk erosion and the transition between the two based on a careful selection of matrix size. Further, these degradation profiles (FIG. 8A, B) provide a direct means for calculating a theoretical critical length (i.e. where a given polymer transitions from surface to bulk erosion) (FIG. 9). In contrast to the original calculations of critical length, which used an Erlang distribution to represent the degradation rate, this new calculation relies on a second order rate expression that can directly account for radial gradients in polymer molecular weight within the matrix. When accounting for the different degradation rates used in these two expressions, both sets of calculated values for critical length agree within order of magnitude for all systems tested.

Figure 10:
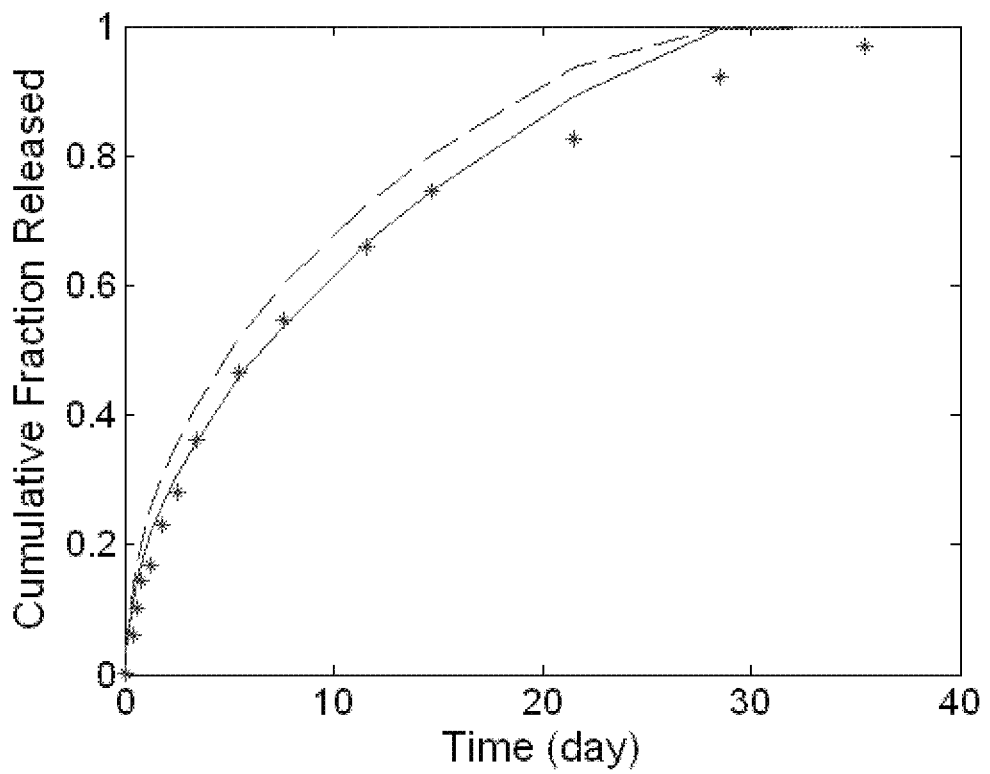
FIG. 10 is a graph showing predictions of dissolution-controlled, release of drug. The experimental data (asterisks) was generated from polyanhydride disks releasing the sparingly soluble agent, bupivacaine. For comparison, model predictions were generated without regression while considering surface erosion (solid, SSE=0.0204), and assuming bulk erosion (dashed, SSE=0.0691). To make these regression-free predictions, system-specific parameters were set as follows: $R_p$=4 mm, L=1 mm, $Mw_o$=50 kDa, $C_{So}$=288.42 mol/m³ and $C_{Amx}$=2.184 mol/m³ $k_{dis}$=0.046 mol/m³ s. D was calculated as 4.61×$10^{-12}$ m²/s from a correlation published previously.

Comparison of predictions from the model to experimental data from biodegradable matrices serves to validate elements of its release paradigm. The bupivacaine-loaded disks modeled in FIG. 10 showcase the importance of the dissolution and hydration rate expressions in generating accurate (SSE=0.0172) predictions for the release of a sparingly soluble agent from a polyanhydride matrix. (FIG. 10) Attempting to predict the release of bupivacaine without considering its slow dissolution produced inaccurate predictions. Conversely, predictions made without considering the system's hydration kinetics show only a slight decrease in model accuracy. Prima facie, it may be surprising that a slight drop in accuracy is observed with this system which, being a bulk eroding system, is most often characterized by rapid, uniform hydration. However, prior work indicates that, while bulk eroding systems in the micron size-range hydrate in minutes, bulk eroding implants (as defined by diffusion rate>degradation rate) on the order of millimeters can take days to become uniformly hydrated.[13] When such an implant only delivers drug over several days or weeks, this longer hydration time can significantly delay release, even though the system can be technically considered "bulk eroding".

Regression-free predictions for the POE matrix (FIG. 12A) provide a different view for the importance of accounting for various mechanisms of matrix dynamics and physical agent egress. Like the bupivacaine-loaded matrix featured in FIG. 10, predictions for this system were also significantly better when hydration kinetics were accounted for by the model. This provides additional support for the conclusion that hydration kinetics can significantly influence the rate of drug release from bulk eroding implants. Unlike dissolution-limited release of bupivacaine, though, the readily-soluble amaranth red being released from this system is instead thought to only be restricted by the POE matrix. Because this system contained an anhydride excipient the model's proven degradation-controlled release paradigm was augmented to account for the consumption of water during anhydride hydrolysis. Attempting to predict release from this system without accounting for the diversion of water into the hydrolysis of the anhydride lead to increased error during middle times, when the anhydride excipient is postulated to be hydrolyzing between 1 and 3 days. (data not shown) Even with this increased error, predictions from the current model still offer an improvement in accuracy (lower SSE) over prior modeling work.

The implants examined in FIG. 11 are slightly larger than the calculated critical length, and gentamicin is large enough to be readily restricted by the polymer matrix, making this a prime example of how release occurs in a system that transitions from surface to bulk erosion. Support of the model paradigm for release from a transitioning system is found in the accurate regression-free prediction (SSE=0.0821) data from this system. (FIG. 11). Failing to consider matrix hydration kinetics greatly (8-fold) decreases the accuracy of this prediction, as would be expected for a system that begins under surface erosion. This change is much more dramatic than the one observed for comparable bulk eroding systems (e.g. FIG. 10), which provides a perspective on the crucial that role hydration kinetics play in systems that transition from surface to bulk erosion.

With respects to the POE controlled release data in FIG. 12B, it is apparent that the simplified form of the model, assuming bulk erosion, generates a more accurate prediction of the amaranth red release data from the disk with 1% anhydride content than the full version of the model, even though the matrix should theoretically begin release under a surface eroding mechanism. However it is important to note that published empirical evidence, from time-lapse images of matrix cross-sections, clearly shows a distinct change in internal morphology, between 5 and 8 hours of incubation, that suggests water has already perfused into the matrix core. This hydration appears to occur much more rapidly than is predicted by equations 6 and 7 (data not shown). During the time period between 5 and 8 hours, the initially rapid, average hydrolysis rate also transitions to a near zero value, which is inconsistent with published predictions based on random chain scission theory. Taken together, this evidence suggests that another process, beyond the diffusion/reaction kinetics considered herein, causes water to perfuse the matrix earlier than expected by simple diffusion and hydrolysis for this system. It is possible that the unaccounted driving force could come from an increase in matrix osmotic pressure, brought about by the 1 w/w % of anhydride excipient. Regardless, this data serves an example of how actual phenomena can create situations with dynamics that extend beyond model assumptions. However, once the correct physical phenomenon has been determined (using cross sectional analysis here), the model will accurately predict release if constrained accordingly.

Together, the validations performed on published release data sets (FIGS. 10-12) confirm that the regression-free predictions appear accurate when the systems in question conform to the model's fundamental assumptions.

Examples

Figure 15:
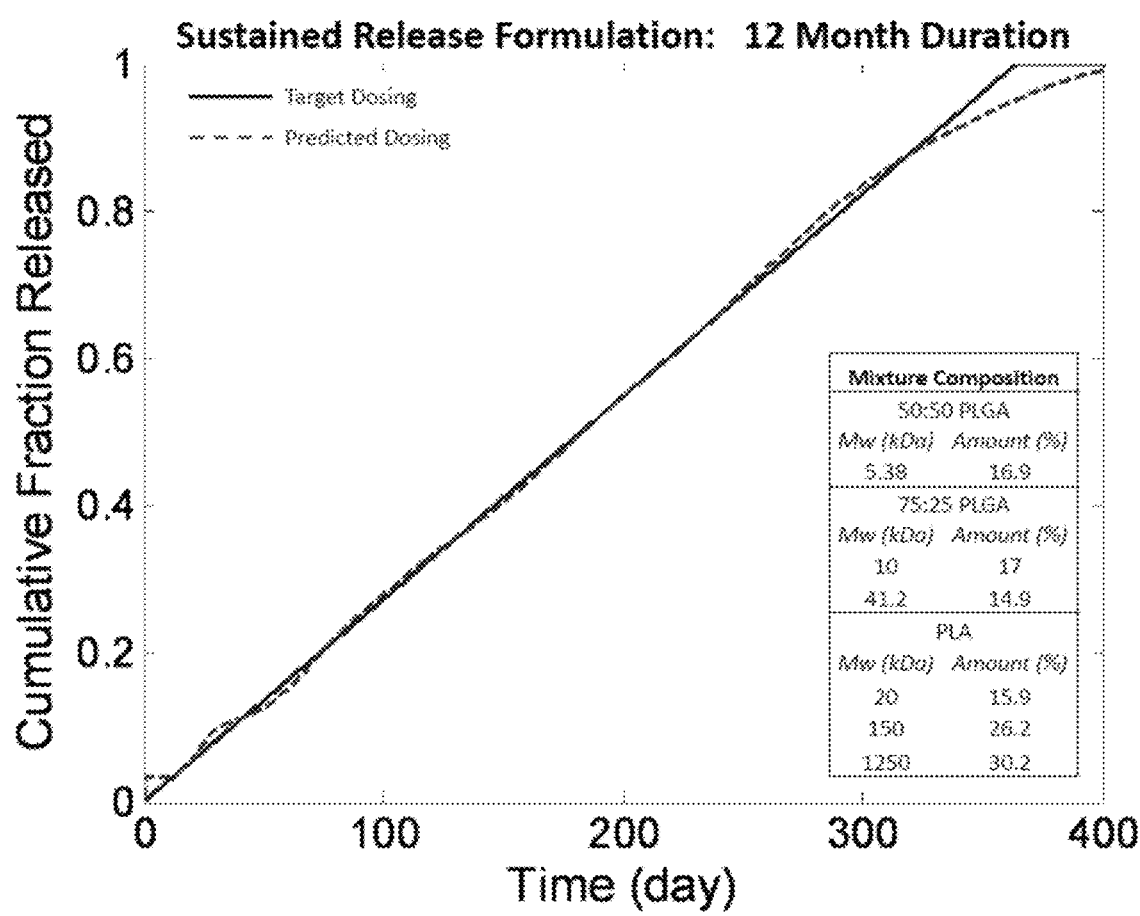

FIGS. 13-16 document the in silico and in vivo development of constant release compositions based on the method described above. Each plot shows cumulative normalized drug release over time for the duration of the formulation's life-span and gives the formulation's composition in the lower right hand corner. Simulations have been conducted to design formulations which sustain macromolecule release for 1, 3 (FIG. 13), 6 (FIG. 14) or 12 months (FIG. 15). A one month formulation (FIG. 16) was also fabricated with the composition below:

| | Microparticles | | |
|---|---|---|---|
| Mwo: | kCw: | Rp: | Rocc: |
| Set 1: 7.4 kDa | 0.08636 day^-1 | >10 um | <0.345*Rp |
| Set 2: 11.3 kDa | 0.08636 day^-1 | >10 um | <0.345*Rp |
| Set 3: 33.1 kDa | 0.08636 day^-1 | >10 um | <0.345*Rp |

The above specifications were confirmed as detailed in the Methods document.

Mwo was specified by the polymer's manufacturer kCw was set by polymer chemistry and was taken from Rothstein 2008 Rp was set at 10 um to preclude the possible that the particles are cleared by phagocytosis Rocc was set to 34.5% of Rp to minimize the initial burst to no more than 10% of total release.

Figure 16:
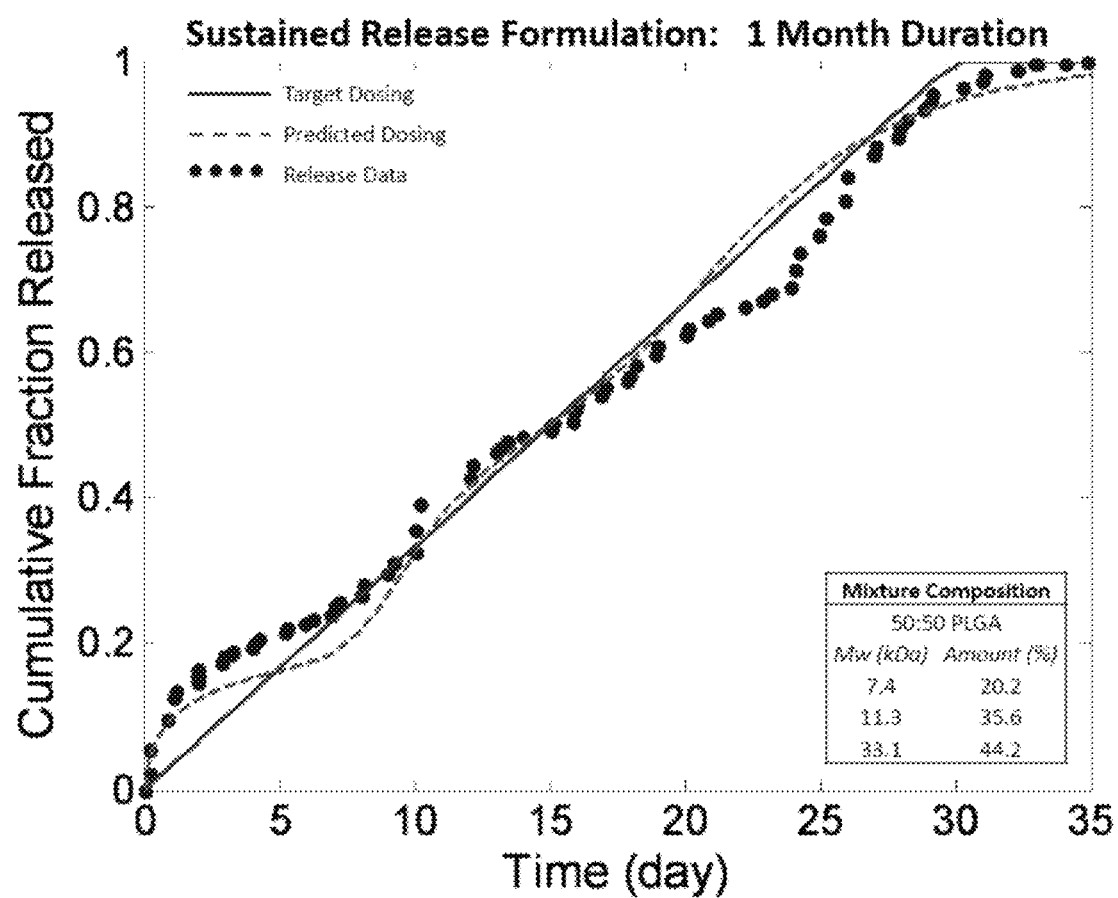
FIG. 16 is a graph depicting the actual release rate compared to target and predicted dosing for a sustained release composition that was prepared according to the methods described herein.

The formulation of FIG. 16 was tested in vitro using a fluorescently labeled dextran as a model therapeutic and the results are shown in FIG. 16.

In view of the many possible embodiments to which the principles of the disclosed compositions and methods may be applied, it should be recognized that the illustrated embodiments are only preferred examples and should not be taken as limiting the scope of the invention.

What is claimed is:

1. A computer-implemented method comprising:
   receiving, by a processor, a dissolution rate for a formulation containing an active agent;
   assessing, by the processor, dissolution rates for sample formulations containing at least one hydrolysable polymer and the active agent based on properties of each of the at least one hydrolysable polymer and properties of the active agent;
   generating, by the processor, a formulation containing the at least one hydrolysable polymer and the active agent, wherein the formulation has a dissolution rate corresponding to the dissolution rate; and
   identifying a formulation, said identifying comprising:
      performing, by the processor, non-linear optimization on one or more formulations to determine the percent total composition of each of the at least one hydrolysable polymer in each formulation;
      eliminating, by the processor, each formulation having the percent total composition of less than 1 percent for at each least one hydrolysable polymer; and
      repeating the step of performing non-linear optimization and eliminating each formulation until a percent change of greater than 5 percent is reached or one formulation remains.

2. The method of claim 1, wherein the properties for each of at least one hydrolysable polymer are selected from the group consisting of initial molecular weights (Mwo) and polymer degradation rates (kCw).

3. The method of claim 1, wherein the formulation defines a composition that is a sustained release pharmaceutical composition.

4. The method of claim 1, wherein the active agent is a bioactive agent or a therapeutic agent.

5. The method of claim 1, wherein each at least one hydrolysable polymer is selected from the group consisting of poly(glycolic acid), poly(lactic acid), poly(lactic-co-glycolic acid), polyanhydride, poly($\alpha$-hydroxy ester), poly($\beta$-hydroxy ester), poly(ortho ester), and mixtures thereof.

6. The method of claim 1, wherein the formulation defines a medicament.

7. The method of claim 6, wherein the medicament is selected from the group consisting of matrix tablets, enteric coated tablets, single and double coated tablets, capsules, minitablets, caplets, coated beads, granules, spheroids, pellets, microparticles, suspensions, topicals, injectables, inhalable compositions, and implants.

8. The method of claim 1, further comprising making a composition based on the formulation.

9. The method of claim 1, wherein the properties of the active agent are selected from an agent's molecular weight (MwA), aqueous solubility, isoelectric point, and combinations thereof.

10. The method of claim 1, wherein predicting a dissolution rate further comprises determining a mean time for pore formation ($\tau$) based on the properties of each at least one hydrolysable polymer.

11. The method of claim 10, further comprising determining a variance ($\sigma^2$) in induction time distribution for pore formation ($\varepsilon(t)$).

12. The method of claim 11, wherein determining the variance ($\sigma^2$) further comprises determining a distribution of polymer degradation rates ($kC_w(n)$) attributed to crystallinity of each at least one hydrolysable polymer.

13. The method of claim 1, wherein predicting the dissolution rate further comprises determining a diffusivity of the active agent (D) from each at least one hydrolysable polymer.

14. The method of claim 1, wherein predicting a dissolution rate further comprises determining a molecular weight at release (Mwr) for each at least one hydrolysable polymer based on the physical properties of the at least one active agent.

15. The method of claim 14, wherein the molecular weight at release (Mwr) is determined based on a molecular weight of the at least active agent (MwA) encapsulated by each at least one hydrolysable polymer.

16. A method of providing a formulation specification to be used for making a modified release composition for delivering an active agent, comprising:
   selecting a desired active agent and polymer;
   determining the desired active agent's molecular weight and aqueous solubility;
   determining a mean time for pore formation for the polymer;
   creating a library of building blocks of formulations from the mean time for pore formation and the desired active agent's molecular weight and aqueous solubility
   determining an optimal ratio of the of the desired active agent and polymer comprising performing a non-linear optimization to compute percent composition of each formulation in the building block library based on a best fit with a specified release profile; eliminating each formulation having the percent composition of less than 1 percent; and
   repeating the nonlinear optimization until a percent change of 5 percent or greater from its original value is reached; and
   providing the formulation specification based on the optimal ratio determination.

* * * * *